US006436997B1

(12) United States Patent
de Tejada

(10) Patent No.: US 6,436,997 B1
(45) Date of Patent: *Aug. 20, 2002

(54) ENDOGENOUS NITRIC OXIDE SYNTHESIS UNDER CONDITIONS OF LOW OXYGEN TENSION

(75) Inventor: Inigo Saenz de Tejada, Madrid (ES)

(73) Assignee: NitroMed, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/429,020

(22) Filed: Oct. 29, 1999

Related U.S. Application Data

(63) Continuation-in-part of application No. PCT/US99/11876, filed on Jun. 1, 1999, and a continuation-in-part of application No. 09/321,584, filed on May 28, 1999, now Pat. No. 6,277,884.
(60) Provisional application No. 60/087,556, filed on Jun. 1, 1998.

(51) Int. Cl.⁷ ............................................. A61K 31/195
(52) U.S. Cl. ...................................................... 514/565
(58) Field of Search ........................................ 514/565

(56) References Cited

U.S. PATENT DOCUMENTS

| 5,594,032 A | 1/1997 | Gonzalez-Cadavid |
| 5,906,987 A | 5/1999 | Chwalisz et al. |

FOREIGN PATENT DOCUMENTS

| WO | 9739760 | 10/1997 |
| WO | 9822479 | 5/1998 |
| WO | 9823267 | 6/1998 |
| WO | 9919295 | 4/1999 |

OTHER PUBLICATIONS

Sills et al, Chemical Abstracts, vol. 105, abstract No. 90990, 1986.*
Sakamaki et al, Chemical Abstracts, vol. 127, abstract No. 60432, 1997.*
Kim et al, *J. Clin. Invest.*, 88:112–118 (1991).
Wallace et al, *J. Med. Chem.*, 34:1746–1748 (1991).
Wallace et al, *Biochem. Biophys. Res. Commun.*, 176(1):528–534 (1991).
Zembowicz et al, *Proc. Natl. Acad. Sci. USA*, 88:11172–11176 (1991).
Fukuto et al, *J. Pharmacol. Exp. Ther.*, 263(2):546–551 (1992).
Fukuto et al, *Biochemical Pharmacology*, 43(3):607–613 (1992).
Gibson et al, *Br. J. Pharmacol.*, 107:715–721 (1992).
Pufahl et al, *Biochemistry*, 31:6822–6828 (1992).
Walder et al, *Br. J. Pharmacol.*, 107:476–480 (1992).
Zembowicz et al, *Biochem. Biophys. Res. Commun.*, 189(2):711–716 (1992).
Zembowicz et al, *Br. J. Pharmacol.*, 107:1001–1007 (1992).
Kim et al, *J. Clin. Invest.*, 91:437–442 (1993).
Olken et al, *Biochemistry*, 32:9677–9685 (1993).
Daghigh et al, *Biochem. Biophys. Res. Commun.*, 202(1):174–180 (1994).
Komori et al, *Arch. Biochem. Biophys.*, 315(2):213–218 (1994).
Schott et al, *FEBS Letters*, 341:203–207 (1994).
Yokoi et al, *Neuropharmacol.*, 33(11):1261–1265 (1994).
Hecker et al, *Proc. Natl. Acad. Sci. USA*, 92:4671–4675 (1995).
Hecker et al, *FEBS Letters*, 359:251–254 (1995).
Abdul–Hussain et al, *Eur. J. Pharmacol.*, 305–155–161 (1996).
Chakder et al, *J. Pharmacol. Exp. Ther.*, 282:378–384 (1997).
Clague et al, *Biochemistry*, 36:14465–14473 (1997).
Modolell et al, *FEBS Letters* 401:123–126 (1997).
Pieper et al, *J. Pharmacol. Exp. Ther.*, 283(2):684–691 (1997).
Vetrovsky et al, *Biochem. Biophys. Acta.*, 1334:51–56 (1997).
Choi et al, *Biochem. Biophys. Res. Commun.*, 246:431–435 (1998).
Grant et al, *Biochemistry*, 37:4174–4180 (1998).
Moali et al, *Biochemistry*, 37:10453–10460 (1998).
Renodon–Corniere A. et al, *Biochemistry*, 38:4663–4668 (1999).
Baggio et al, *Journal of the American Chemical Society*, 119(34):8107–8108, (Apr. 25, 1997).
Sakamaki et al, Kitakanto Med. J., 47(3) :133–139 (1997).
Sills et al, Thrombosis and Haemostasis, 55 (3) :305–308 (1986).

\* cited by examiner

*Primary Examiner*—William R. A. Jarvis
(74) *Attorney, Agent, or Firm*—Hale and Dorr LLP

(57) ABSTRACT

The present invention provides methods of promoting synthesis of nitric oxide or endothelium-derived relaxing factor (EDRF) in hypoxic mammalian tissues by administering at least one N-hydroxyguanidine compound that is a substrate of nitric oxide synthase, and, optionally, one or more vasoactive agents and/or thromboxane A2 receptor antagonists. The present invention also provides methods of promoting vasorelaxation and treating sexual dysfunctions in patients by administering at least one N-hydroxyguanidine compound that is a substrate for nitric oxide synthase, and, optionally, at least one vasoactive agent and/or thromboxane A2 receptor antagonist. The present invention also provides methods for treating clinical conditions resulting from hypoxic conditions such as pulmonary disease, cardiovascular disorders, circulatory hypoxia, specific organ hypoxia, localized hypoxia, edema, central nervous system disorders, memory loss, or arterial disease. The present invention also provides methods for treating clinical conditions resulting from an abnormally high level of arginase activity, such as, heart disease, systemic hypertension, pulmonary hypertension, sexual dysfunction, autoimmune disease, chronic renal failure and cerebral vasospasm. The present invention also provides methods for treating clinical conditions associated with a deficient nitric oxide pathway by administering at least one N-hydroxyguanidine compound and, optionally, one or more vasoactive agents and/or thromboxane A2 receptor antagonists. The present invention also provides pharmaceutical compositions comprising at least one N-hydroxyguanidine compound, and, optionally, one or more vasoactive agents and/or thromboxane A2 receptor antagonists.

49 Claims, 21 Drawing Sheets

ENDOGENOUS NITRIC OXIDE SYNTHESIS UNDER CONDITIONS OF LOW OXYGEN TENSION

This is a continuation-in-part of PCT Application No. PCT/US99/11876, filed Jun. 1, 1999, and U.S. application Ser. No. 09/321,584, filed May 28, 1999, now U.S. Pat. No. 6,277,884 both of which claim priority to U.S. Provisional Application No. 60/087,556, filed Jun. 1, 1998.

FIELD OF THE INVENTION

The present invention describes novel methods to induce synthesis of endogenous nitric oxide or endothelium-derived relaxing factor, and methods for maintaining levels of nitric oxide under hypoxic conditions. One aspect of the invention relates to novel methods to induce vasodilation. The present invention also provides methods for treating or preventing sexual dysfunctions in males and females by administering at least one N-hydroxyguanidine compound, such as N-hydroxy-L-arginine, and, optionally, one or more vasoactive agents and/or thromboxane A2 receptor antagonists. The present invention also provides methods for treating clinical conditions resulting from hypoxic conditions, such as, pulmonary diseases, cardiovascular disorders, circulatory hypoxia, specific organ hypoxia, localized hypoxia, edema, central nervous system disorders, memory loss and/or arterial disease. The present invention also provides methods for treating clinical conditions resulting from an abnormally high level of arginase activity, such as, heart diseases, systemic hypertension, pulmonary hypertension, sexual dysfunctions, autoimmune diseases, chronic renal failure and/or cerebral vasospasm. The present invention also provides methods for treating clinical conditions associated with a deficient nitric oxide pathway by administering at least one N-hydroxyguanidine compound, and, optionally, one or more vasoactive agents and/or thromboxane A2 receptor antagonists. The present invention also provides novel compositions comprising at least one N-hydroxyguanidine, and optionally, one or more vasoactive agents and/or thromboxane A2 receptor antagonists. The N-hydroxyguanidine compounds in the present invention are substrates for nitric oxide synthase.

BACKGROUND OF THE INVENTION

Nitric oxide is a small diatomic molecule with multiple biological actions, including inhibition of platelet adhesion and aggregation, and relaxation of vascular and non-vascular smooth muscles. Nitric oxide has also been reported to have antiinflammatory, anti-bacterial and anti-viral properties (Moncada et al, *Pharmacol Rev.* 43:109–142 (1991)). In the gaseous state nitric oxide exists as a lipophilic molecule in a neutral redox state (NO). Nitric oxide is a complex molecule since it is able to exist in multiple redox states under different physiological conditions. It can also formally exist in charged forms i.e., nitrosonium ($NO^+$) or nitroxyl ($NO^-$), or as the neutral species, nitric oxide (NO•). In biological tissues, nitric oxide has a very short half-life, estimated at less than one second.

One of the potent actions of nitric oxide in mammals is to relax vascular and non-vascular tissue, and, as such, either nitric oxide or an adduct that delivers nitric oxide, is useful as a vasodilator. In the mammalian body, endogenous nitric oxide is produced through an enzymatic reaction in which nitric oxide synthases utilize L-arginine and molecular oxygen for the synthesis of nitric oxide and citrulline. One of the actions of nitric oxide is believed to be the activation of a soluble form of guanylate cyclase, a cellular enzyme, which catalyses the formation of 3',5'-cyclic guanosine monophosphate (cGMP). The cGMP is believed to act on other cellular targets to mediate the relaxation of vascular smooth muscle and provide the therapeutic effect of vasodilation. Another action of nitric oxide is believed to be the regulation of $Na^{(+)}$-$K^{(+)}$-ATPase.

The synthesis of nitric oxide from L-arginine by nitric oxide synthase occurs in two steps, each of which requires NADPH. In the first step, an intermediate N-hydroxyguanidine product, $N^G$-hydroxy-L-arginine, is synthesized by the incorporation of an oxygen into the guanidine function of the L-arginine molecule. In the second step, a second oxygen is incorporated into $N^G$-hydroxy-L-arginine to form L-citrulline and nitric oxide. (Fukuto et al, in *Methods in Nitric Oxide Research*, Feelisch et al, eds., John Wiley & Sons, Ltd., pp. 147–160 (1996)). Under an environment of low oxygen tension, however, the synthesis of nitric oxide is greatly reduced. (Furchgott et al, *Nature*, 288(5789):373–376 (1980); Johns et al, *Circ. Res.*, 65(6):1508–1515 (1989)).

Several clinical conditions are associated with low oxygen tension, such as sexual dysfunctions (Kim et al, *J. Clin. Invest.* 91(2):437–442 (1993)), pulmonary diseases (including respiratory distress syndrome, asthma, bronchitis/emphysema, and chronic obstructive pulmonary disease) (Howes et al, *Thorax*, 51(5):516–519, (1996); Fagan et al, *Biochem. Biophys. Res. Commun.* 254(1):100–103 (1999)), circulatory hypoxia (including heart failure, strokes, and shock), specific organ hypoxia (in which decreased circulation to a specific organ resulting in localized circulatory hypoxia can be due to organic arterial obstruction or can result as a consequence of vasoconstriction, e.g., Raynaud's Syndrome) (Agusti et al, *Eur. Rspir. J.* 10(9):1962–1966 (1997)), localized hypoxia (which can result from venous obstruction and resultant congestions and reduced arterial blood inflow), edema (which increases the distance through which oxygen diffuses before it reaches the cells can also cause localized hypoxia), central nervous system disorders, memory loss, and arterial disease (Weitzberg et al, *Acta. Physiol. Scand.* 143(4):451–452 (1991)).

Respiratory distress syndrome, in a child or adult, has severe consequences in the vasculature, such as pulmonary hypertension. Arterial insufficiency of the blood vessel of the penis leads to hypoxic ischemia of this tissue, which limits the synthesis of nitric oxide and, therefore, limits the erectile capacity.

Increased oxygen requirements can also lead to low oxygen tension. For example, if the oxygen consumption of a tissue is elevated without a corresponding increase in volume flow per unit time, then the oxygen tension ($Pa_{O2}$) in the venous blood can be reduced. This can also occur when the hemoglobin is qualitatively and quantitative normal. Examples of such situations include fever and thyrotoxicosis in which cardiac output cannot rise normally, and also in cases in which metabolic rates of oxygen consumption are high.

It would be desirable to increase the production of nitric oxide in tissue under low oxygen conditions to activate the chain of biochemical and cellular events that lead to vasodilation. The present invention is directed to these, as well as other, important ends.

SUMMARY OF THE INVENTION

It has been discovered that administering one or more N-hydroxyguanidine compounds that are substrates for nitric oxide synthase, such as N-hydroxy-L-arginine, to tissues under conditions of low oxygen tension (hypoxia), results in the synthesis of nitric oxide, which is more effective than arginine in promoting the formation of cGMP and the relaxation of vascular and non-vascular smooth muscles.

One embodiment of the invention provides methods of promoting synthesis of nitric oxide in vascular and non-vascular cells of a mammal under low oxygen conditions comprising administering to the mammal a therapeutically effective amount of at least one N-hydroxyguanidine compound, such as N-hydroxy-L-arginine, and, optionally, at least one vasoactive agent and/or at least one thromboxane A2 receptor antagonist.

Another embodiment of the invention provides methods of promoting relaxation of vascular and non-vascular smooth muscle in a mammalian tissue under low oxygen conditions comprising administering to the patient a therapeutically effective amount of at least one N-hydroxyguanidine compound, such as N-hydroxy-L-arginine, and, optionally, at least one vasoactive agent and/or at least one thromboxane A2 receptor antagonist.

Another embodiment of the invention provides methods of treating sexual dysfunctions in patients, including males and females, comprising administering to the patient a therapeutically effective amount of at least one N-hydroxyguanidine compound, such as N-hydroxy-L-arginine, and, optionally, at least one vasoactive agent and/or at least one thromboxane A2 receptor antagonist. Generally, the sexual dysfunction is attributable to low oxygen conditions. Preferably, the sexual dysfunctions are attributable to hypoxic ischemia, neuropathy or arterial disease.

Another embodiment of the invention provides methods of promoting synthesis of nitric oxide or endothelium-derived relaxing factor (EDRF) in hypoxic mammalian cells (low oxygen conditions) comprising administering to the patient a therapeutically effective amount of at least one N-hydroxyguanidine compound, such as N-hydroxy-L-arginine, and, optionally, at least one vasoactive agent and/or at least one thromboxane A2 receptor antagonist.

Another embodiment of the invention provides methods to treat clinical conditions associated with low oxygen tension, such as, pulmonary diseases, circulatory hypoxia, specific organ hypoxia, localized hypoxia, edema, central nervous system disorders, memory loss or arterial disease, comprising administering to a patient in need thereof a therapeutically effective amount of at least one N-hydroxyguanidine compound, such as N-hydroxy-L-arginine, and, optionally, at least one vasoactive agent and/or at least one thromboxane A2 receptor antagonist.

Another embodiment of the invention provides methods to treat clinical conditions associated with an abnormally high level of arginase activity, such as, heart disease, systemic hypertension, sexual dysfunctions, pulmonary hypertension, autoimmune diseases, chronic renal failure and cerebral vasospasm, comprising administering to a patient in need thereof a therapeutically effective amount of at least one N-hydroxyguanidine compound, such as N-hydroxy-L-arginine, and, optionally, at least one vasoactive agent and/or at least one thromboxane A2 receptor antagonist.

Another embodiment of the invention provides methods to promote the synthesis of nitric oxide or endothelium-derived relaxing factor in mammals with deficient nitric oxide pathways comprising administering to the patient a therapeutically effective amount of at least one N-hydroxyguanidine compound, such as N-hydroxy-L-arginine, and, optionally, at least one vasoactive agent and/or at least one thromboxane A2 receptor antagonist.

Another embodiment of the invention provides therapeutic compositions comprising at least one N-hydroxyguanidine compound, such as N-hydroxy-L-arginine, and a pharmaceutically acceptable carrier, and, optionally, at least one vasoactive agent and/or at least one thromboxane A2 receptor antagonist. The compositions can also comprise an analog of N-hydroxy-L-arginine, and/or other active compounds.

These and other aspects of the present invention are described in more detail herein.

[4,3,a]quinoxalin-1-one, an inhibitor of soluble guanylate cyclase), are effective to inhibit N-hydroxy-L-arginine induced relaxation of corpus cavernosal tissue under normoxia conditions. Tissues were incubated in physiological salt solution and bubbled with 20% $O_2$ and were treated with increasing concentrations of N-hydroxy-L-arginine in the presence of vehicle alone (Control, open circles), 0.1 mM L-NNA (closed circles) or 0.02 mM ODQ (closed triangles). In the x-axis, log M [N-hydroxy-L-arginine] corresponds to ten fold increases of N-hydroxy-L-arginine from 1 $\mu$M (at −6) to 1000 $\mu$M (at −3). The relaxation of four samples of tissue were measured for each condition shown (n=4). Data are expressed as mean±standard mean error of the percentage of total relaxation induced by 0.1 mM papaverine. *P<0.01 by AVONA analysis.

Figure 4A:
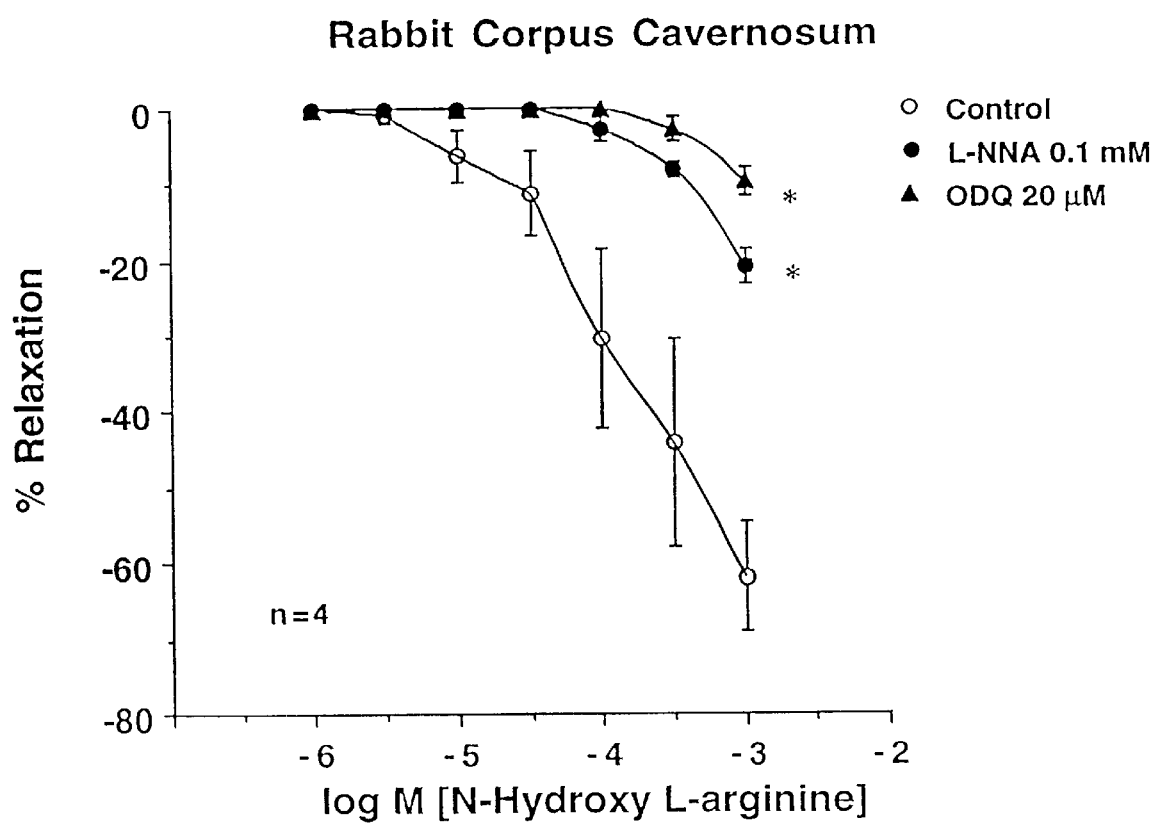
FIG. 4A shows that two different inhibitors of corporal tissue relaxation, L-NNA ($N^G$-nitro-L-arginine, a nitric oxide synthase inhibitor) and ODQ (1H-[1,2,4]-oxadiazolo
Figure 4B:
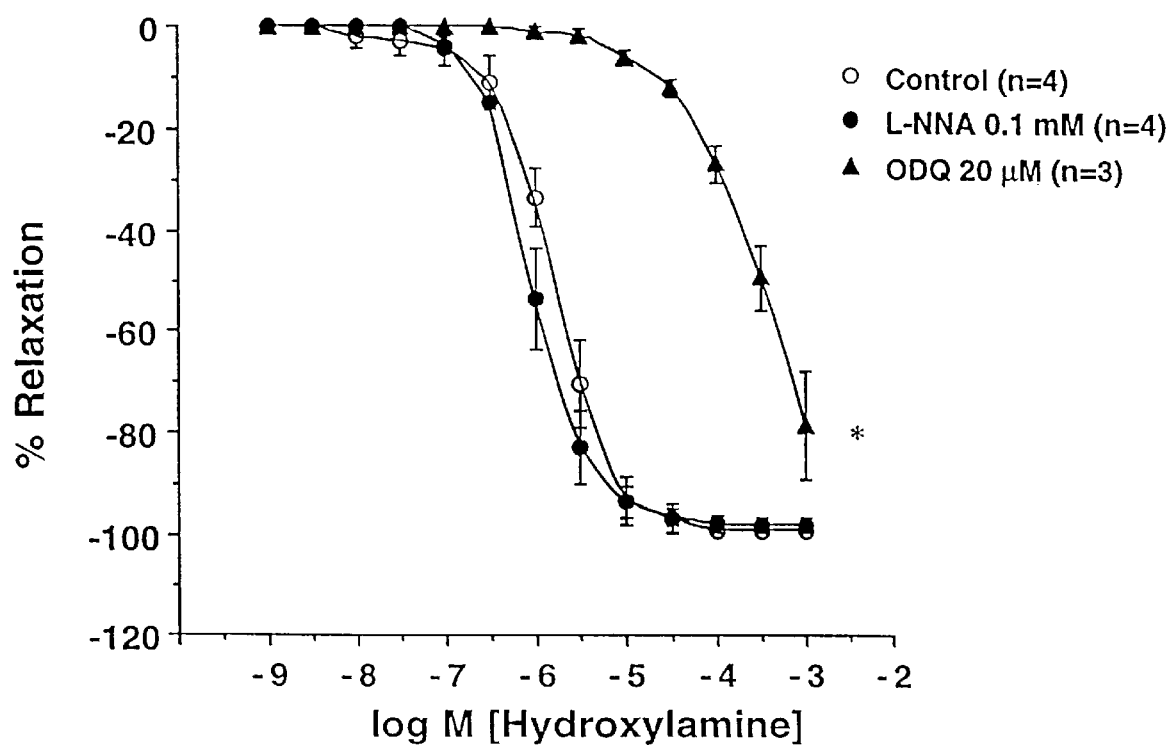

FIG. 4B shows the effect of two different inhibitors of corporal tissue relaxation, L-NNA (a nitric oxide synthase inhibitor) and 1H-[1,2,4]-oxadiazolo[4,3,a]quinoxalin-1-one (ODQ, an inhibitor of soluble guanylate cyclase), on the hydroxylamine induced relaxation of corpus cavernosal tissue under normoxia conditions. Only ODQ inhibits hydroxylamine induced relaxation of corpus cavernosal tissue under normoxia conditions. Tissues were incubated in physiological salt solution and bubbled with 20% $O_2$ and were treated with increasing concentrations of hydroxylamine in the presence of vehicle alone (Control, open circles) where a total of 4 samples were tested (n=4); 0.1 mM L-NNA (closed circles) where a total of 4 samples were tested (n=4); or 0.02 mM ODQ (closed triangles) where a total of 3 samples were tested (n=3);. In the x-axis, log M [hydroxylamine] corresponds to ten fold increases of N-hydroxy-L-arginine from 1 nM (at −9) to 1000 $\mu$M (at −3). Data are expressed as mean±standard mean error of the percentage of total relaxation induced by 0.1 mM papaverine. *P<0.01 by AVONA analysis.

Figure 5A:
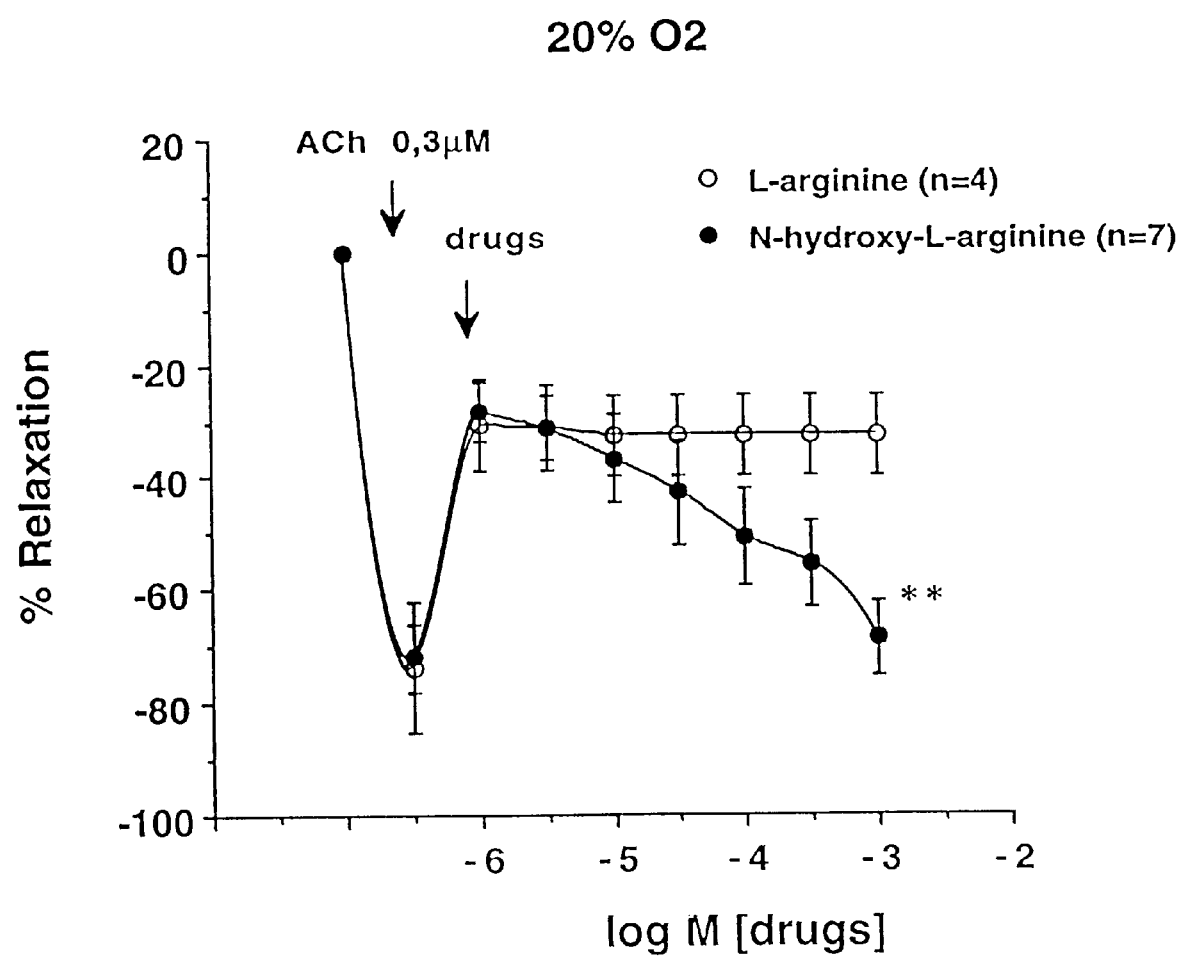

FIG. 5A shows that N-hydroxy-L-arginine is more potent than L-arginine to induce corpus cavernosum tissue relaxation under normoxia conditions. Tissues were incubated in physiological salt solution and bubbled with 20% $O_2$. Each sample was stimulated to relax by administration of 0.3 $\mu$M acetylcholine, and, after the tissue was allowed to recover, various concentrations of either L-arginine (open circles) where a total of 4 samples were tested (n=4); or N-hydroxy-L-arginine (closed circles) where a total of 7 samples were tested (n=7) were administered and the relaxation of the tissue was again measured. In the x-axis, log M [drugs] corresponds to ten fold increases of either L-arginine or N-hydroxy-L-arginine from 1 $\mu$M (at −6) to 1000 $\mu$M (at −3). Data are expressed as mean±standard mean error of the percentage of total relaxation induced by 0.1 mM papaverine. **P<0.01 by AVONA analysis.

Figure 5B:
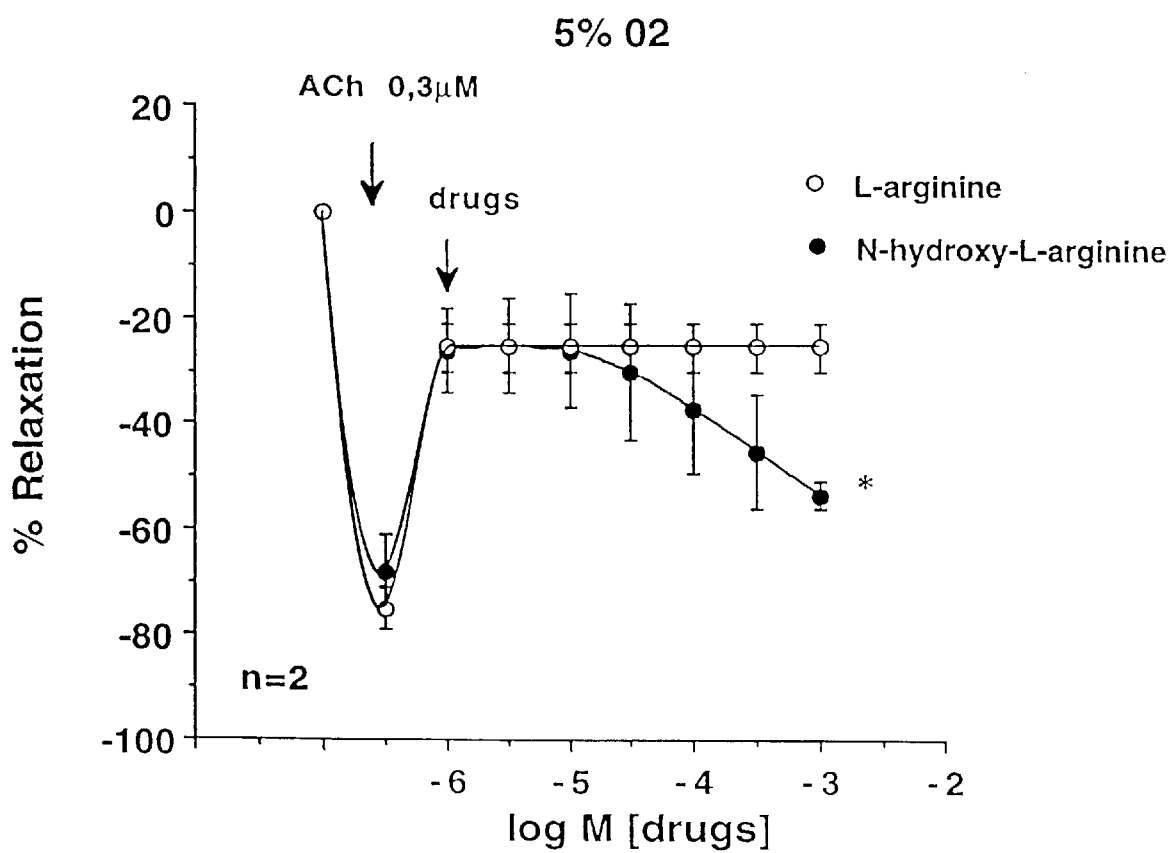

FIG. 5B shows that N-hydroxy-L-arginine is a more potent than L-arginine to induce corpus cavernosum tissue relaxation under hypoxic conditions. Tissues were incubated in physiological salt solution and bubbled with 5% $O_2$. Each sample was stimulated to relax by administration of 0.3 $\mu$M acetylcholine, and, after the tissue was allowed to recover, various concentrations of either L-arginine (open circles) or N-hydroxy-L-arginine (closed circles) were administered and the relaxation of the tissue was again measured. In the x-axis, log M [drugs] corresponds to ten fold increases of either L-arginine or N-hydroxy-L-arginine from 1 $\mu$M (at −6) to 1000 $\mu$M (at −3). The relaxation of two samples of tissue were measured for each condition shown (n=2). Data are expressed as mean±standard mean error of the percentage of total relaxation induced by 0.1 mM papaverine. *P<0.05% by AVONA analysis.

Figure 6:
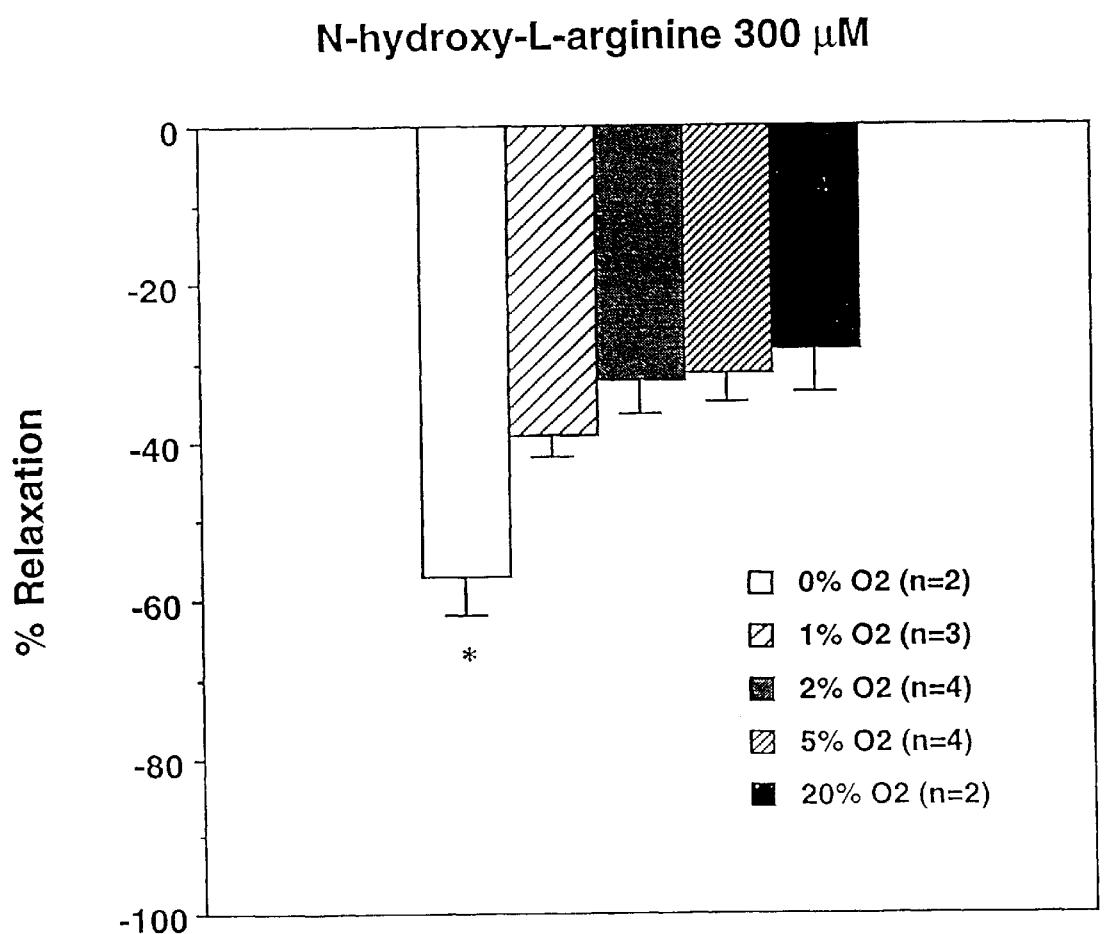

FIG. 6 shows that N-hydroxy-L-arginine is effective to induce relaxation of corpus cavernosum tissue under various oxygen concentrations. Tissues were incubated in physiological salt solution and bubbled with the indicated concentration of $O_2$. 0% oxygen, open bars, total samples tested=2. 1% oxygen, hatched bars, total samples tested=3. 2% oxygen, shaded bars, total samples tested=4. 5% oxygen, densely hatched bars, total samples tested=4. 20% oxygen, filled bars, total samples tested=2. *P<0.05 compared to 20% oxygen by one way AVONA analysis followed by Student Newmann-Keuls post-hoc test.

Figure 7A:
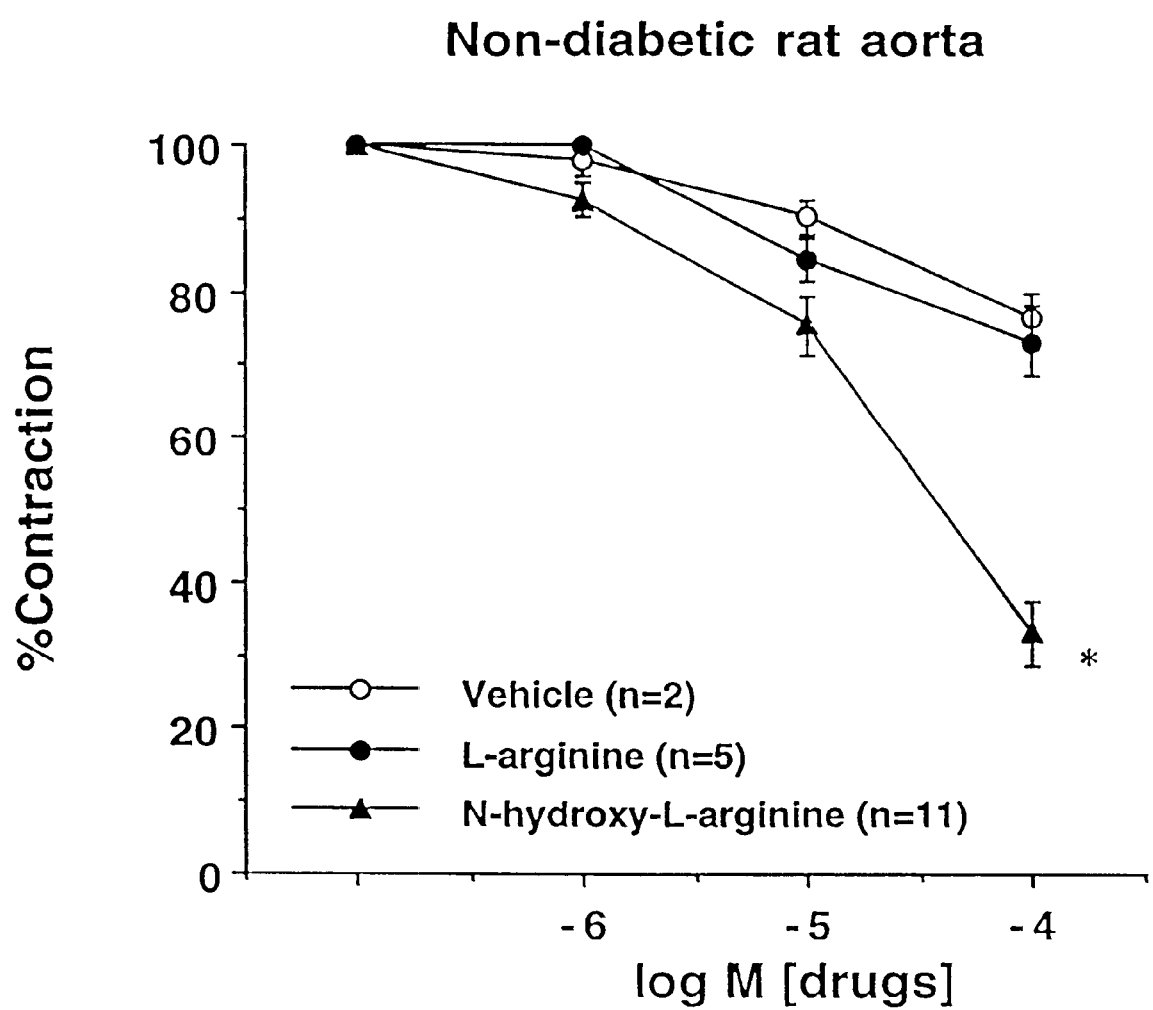

FIG. 7A shows that under normoxia conditions N-hydroxy-L-arginine is more potent than L-arginine to induce relaxation of aortic segments obtained from non-diabetic rats. Tissues were incubated in physiological salt solution and bubbled with 95% $O_2$ and were treated vehicle alone (open circles) where a total of 2 samples were tested (n=2); L-arginine (closed circles) where a total of 5 samples were tested (n=5); or N-hydroxy-L-arginine(closed triangles) where a total of 11 samples were tested (n=11). In the x-axis, log M [drugs] corresponds to ten fold increases of either L-arginine or N-hydroxy-L-arginine from 100 nM (at −7) to 100 $\mu$M (at −4). Data are expressed as mean±standard mean error of the percentage of total relaxation induced by 10 nM norepinephrine. *P<0.01 compared to L-arginine by AVONA analysis.

Figure 7B:
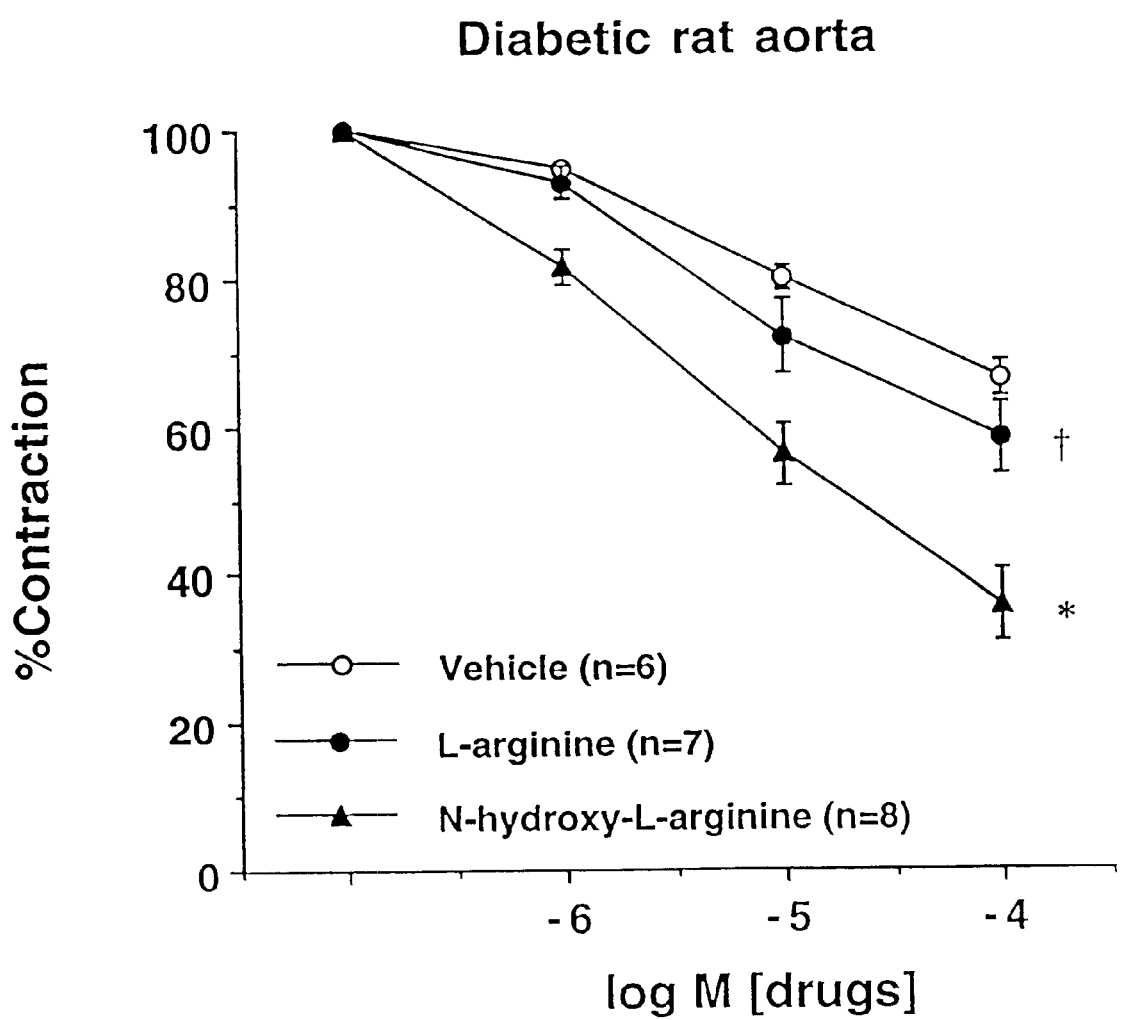

FIG. 7B shows that under normoxia conditions N-hydroxy-L-arginine is more potent than L-arginine to induce relaxation of aortic segment obtained from diabetic rats. Tissues were incubated in physiological salt solution and bubbled with 95% $O_2$ and were treated with vehicle alone (open circles) where a total of 6 samples were tested (n=6);, or L-arginine (closed circles) where a total of 7 samples were tested (n=7); or N-hydroxy-L-arginine (closed triangles) where a total of 8 samples were tested (n=8). In the x-axis, log M [drugs] corresponds to ten fold increases of either L-arginine or N-hydroxy-L-arginine from 100 nM (at −7) to 100 $\mu$M (at −4). Data are expressed as mean±standard mean error of the percentage of total relaxation induced by 10 nM norepinephrine. ↑P<0.05 compared to vehicle and *P<0.01 compared to L-arginine by AVONA analysis.

Figure 8:
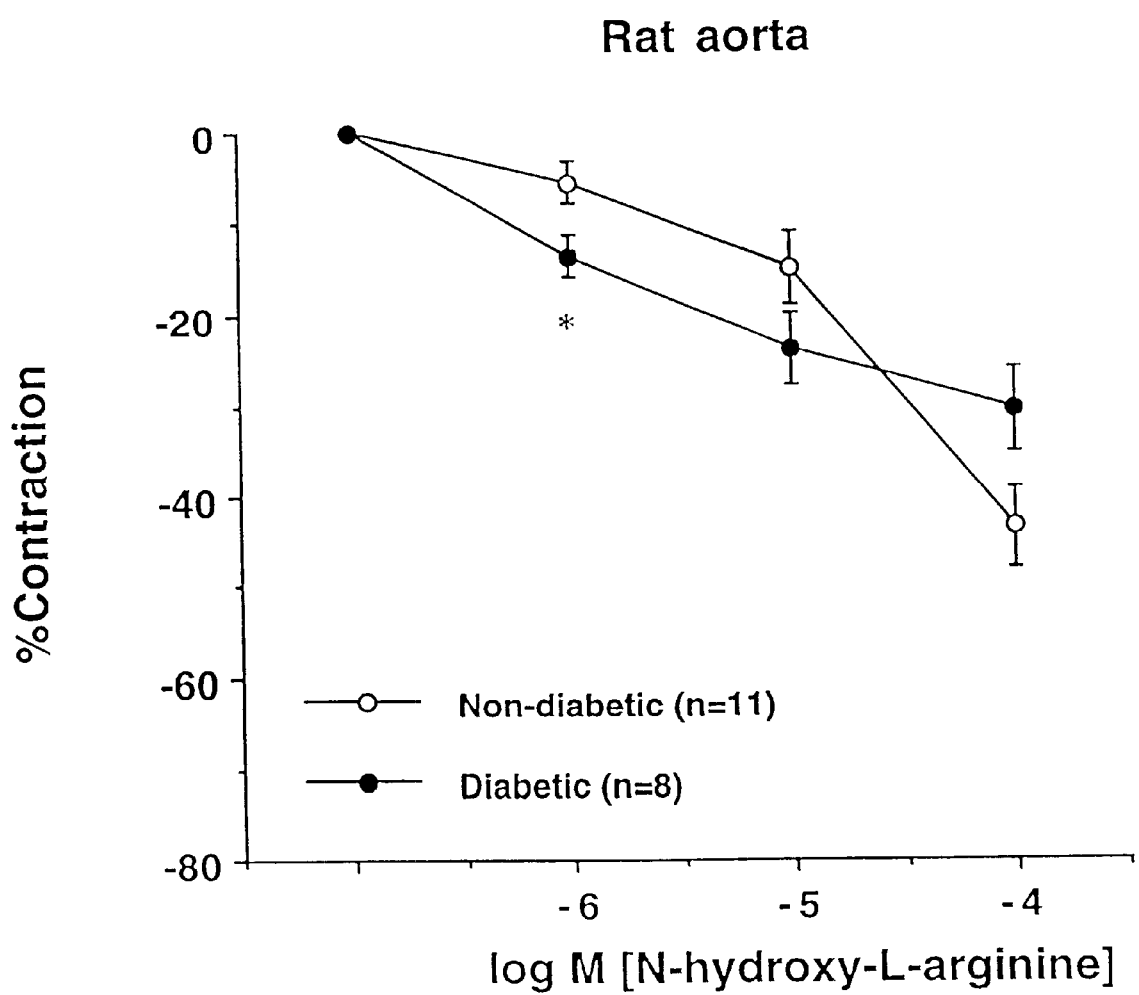

FIG. 8 shows that under normoxia conditions N-hydroxy-L-arginine is more effective in inducing the relaxation of aortic segments obtained from diabetic rats than those obtained from non-diabetic rats. Tissues were incubated in physiological salt solution and bubbled with 95% $O_2$ and were treated with increasing concentrations of N-hydroxy-L-arginine. At lower concentrations of N-hydroxy-L-arginine (1 $\mu$M) the tissue from diabetic rats (closed circles, total samples tested n=8) showed more relaxation than the tissue from non-diabetic rats (open circles, total samples tested n=11). In the x-axis, log M [N-hydroxy-L-arginine] corresponds to ten fold increases of N-hydroxy-L-arginine from 100 nM (at −7) to 100 $\mu$M (at −4). Data are expressed as mean±standard mean error of the percentage of total relaxation induced by 10 nM norepinephrine. *P<0.05 by one way AVONA analysis followed by Student Newmann-Keuls post-hoc test.

Figure 9A:
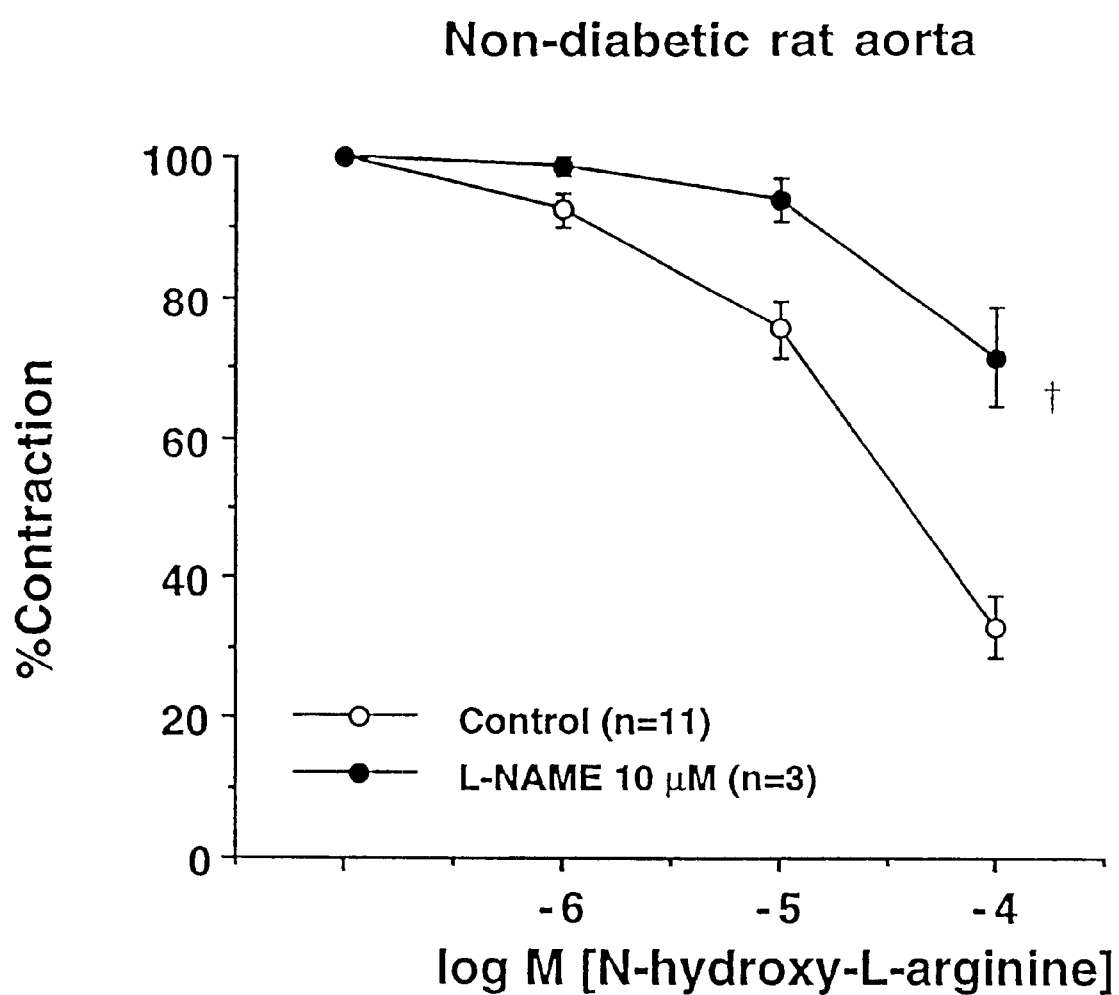

FIG. 9A shows that under normoxia conditions L-NAME ($N^G$-nitro-L-arginine methyl ester, a nitric oxide synthase inhibitor) is effective to inhibit N-hydroxy-L-arginine induced relaxation of aortic rings isolated from non-diabetic rats. Tissues were incubated in physiological salt solution and bubbled with 95% $O_2$ and were treated with increasing concentrations of N-hydroxy-L-arginine in the presence of vehicle alone (Control, open circles, total samples tested n=11) or 10 $\mu$M L-NNA (closed circles, total samples tested, n=3). In the x-axis, log M [N-hydroxy-L-arginine] corresponds to ten fold increases of N-hydroxy-L-arginine from 100 nM (at −7) to 100 μM (at −4). Data are expressed as mean±standard mean error of the percentage of total relaxation induced by 10 nM norepinephrine. *P<0.01 by AVONA analysis.

Figure 9B:
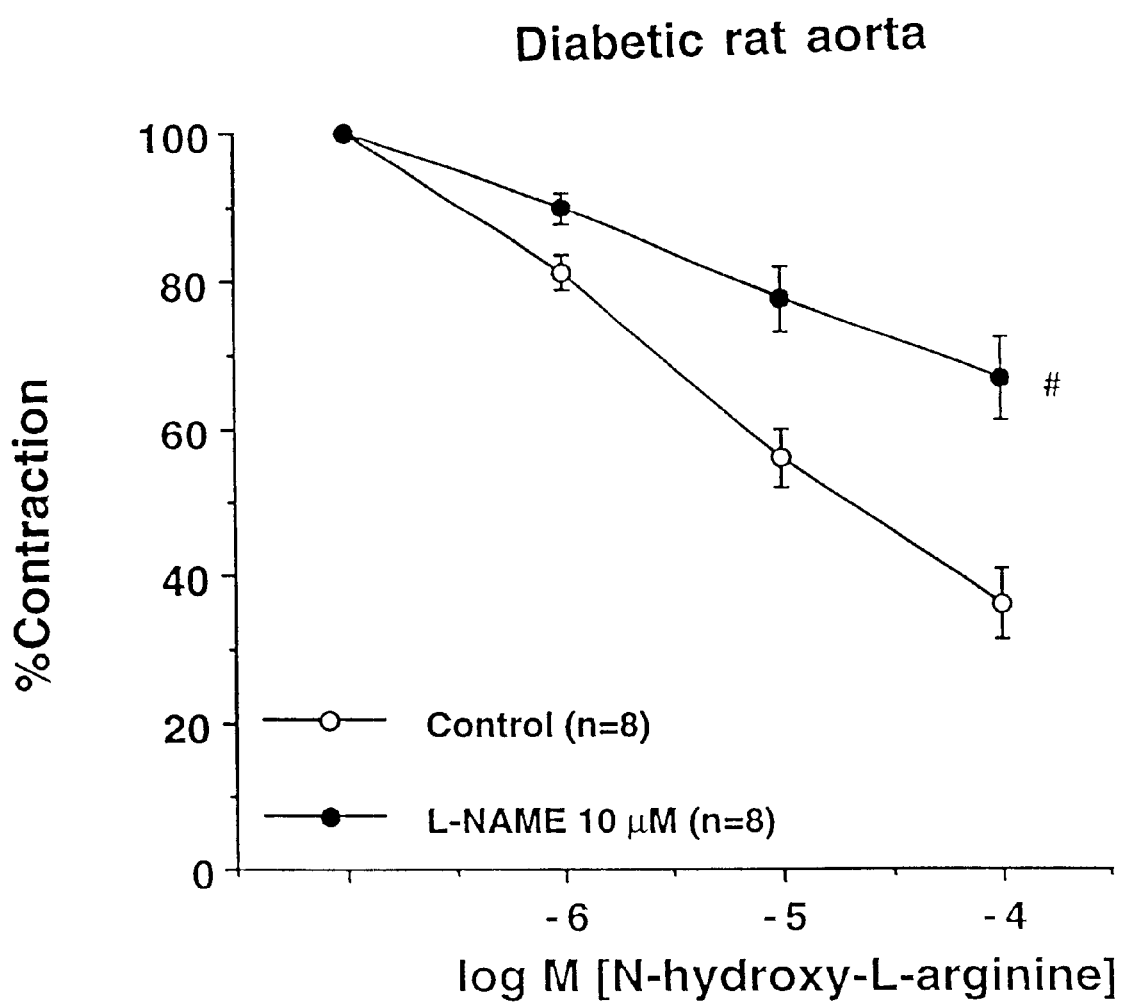

FIG. 9B shows that under normoxia conditions L-NAME ($N^G$-nitro-L-arginine methyl ester, a nitric oxide synthase inhibitor) is effective to inhibit N-hydroxy-L-arginine induced relaxation of aortic rings isolated from diabetic rats. Tissues were incubated in physiological salt solution and bubbled with 95% $O_2$ and were treated with increasing concentrations of N-hydroxy-L-arginine in the presence of vehicle alone (Control, open circles, total samples tested n=8) or 10 μM L-NNA (closed circles, total samples tested, n=8). In the x-axis, log M [N-hydroxy-L-arginine] corresponds to ten fold increases of N-hydroxy-L-arginine from 100 nM (at −7) to 100 μM (at −4). Data are expressed as mean±standard mean error of the percentage of total relaxation induced by 10 nM norepinephrine. #P<0.01 compared to control by AVONA analysis.

Figure 10A:
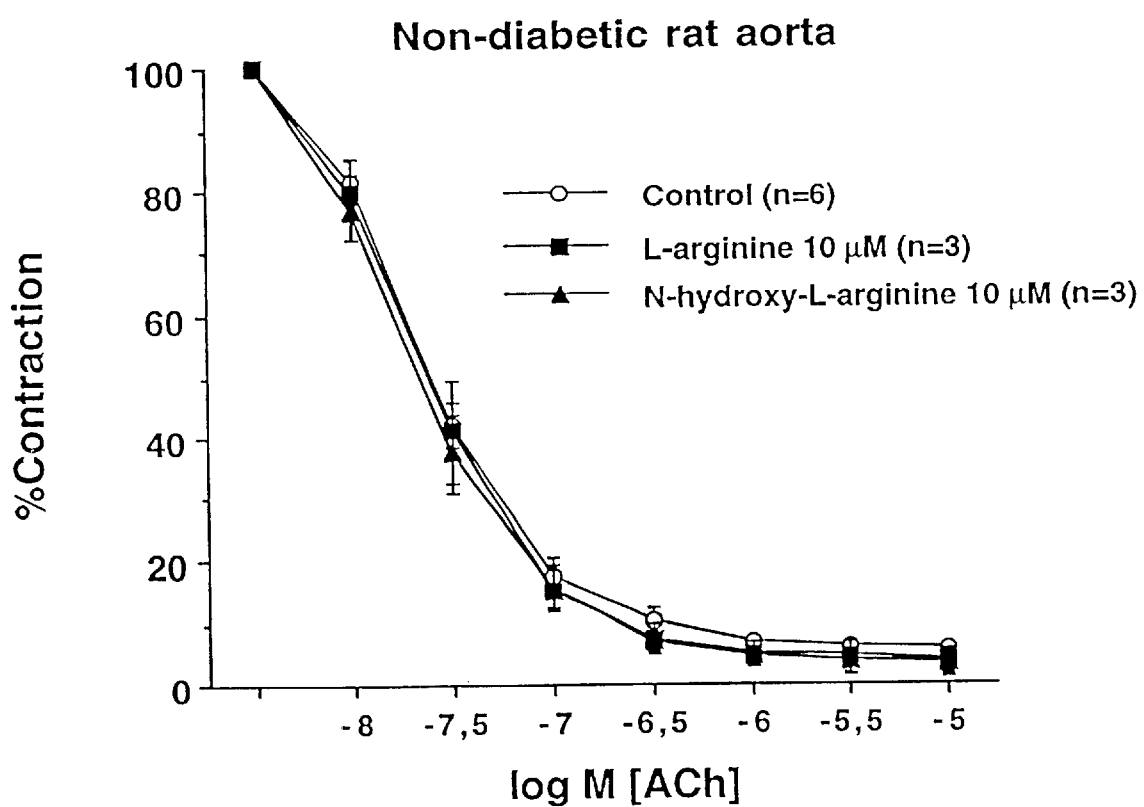

FIG. 10A shows that in the presence of increasing concentrations of ACh under normoxia conditions L-arginine and N-hydroxy-L-arginine do not effect the relaxation of aortic rings isolated from non-diabetic rats. Tissues were incubated in physiological salt solution and bubbled with 20% $O_2$ and were treated with vehicle alone (Control, open circles, total samples tested n=6); or 10 μM L-arginine (closed circles, total number of samples tested n=3) or 10 μM N-hydroxy-L-arginine (closed triangles, total number of samples tested n=3) in the presence of ACh. In the x-axis, log M [ACh] corresponds to ten fold increases of acetylcholine from 10 nM (at −8) to 10 μM (at −5). Data are expressed as mean±standard mean error of the percentage of total relaxation induced by 0.1 mM norepinephrine.

Figure 10B:
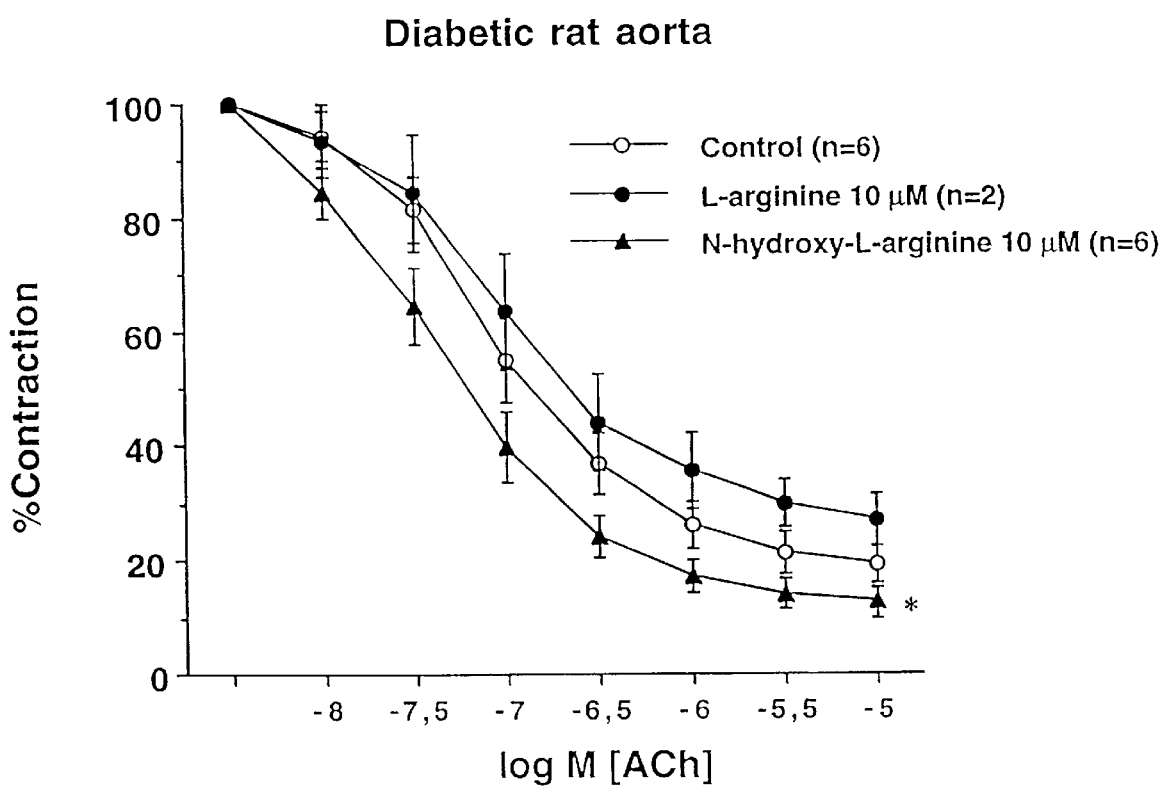

FIG. 10B shows that under normoxia conditions N-hydroxy-L-arginine is more effective than L-arginine in the presence of increasing concentrations of ACh to induce the relaxation of aortic segments isolated from diabetic rats. Tissues were incubated in physiological salt solution and bubbled with 20% $O_2$ and were treated with vehicle alone (Control, open circles, total samples tested n=6); or 10 μM L-arginine (closed circles, total number of samples tested n=2) or 10 μM N-hydroxy-L-arginine (closed triangles, total number of samples tested n=6) in the presence of ACh. In the x-axis, log M [ACh] corresponds to ten fold increases of acetylcholine from 10 nM (at −8) to 10 μM (at −5). Data are expressed as mean±standard mean error of the percentage of total relaxation induced by 0.1 mM norepinephrine. *P<0.01 compared to control by AVONA analysis.

Figure 11A:
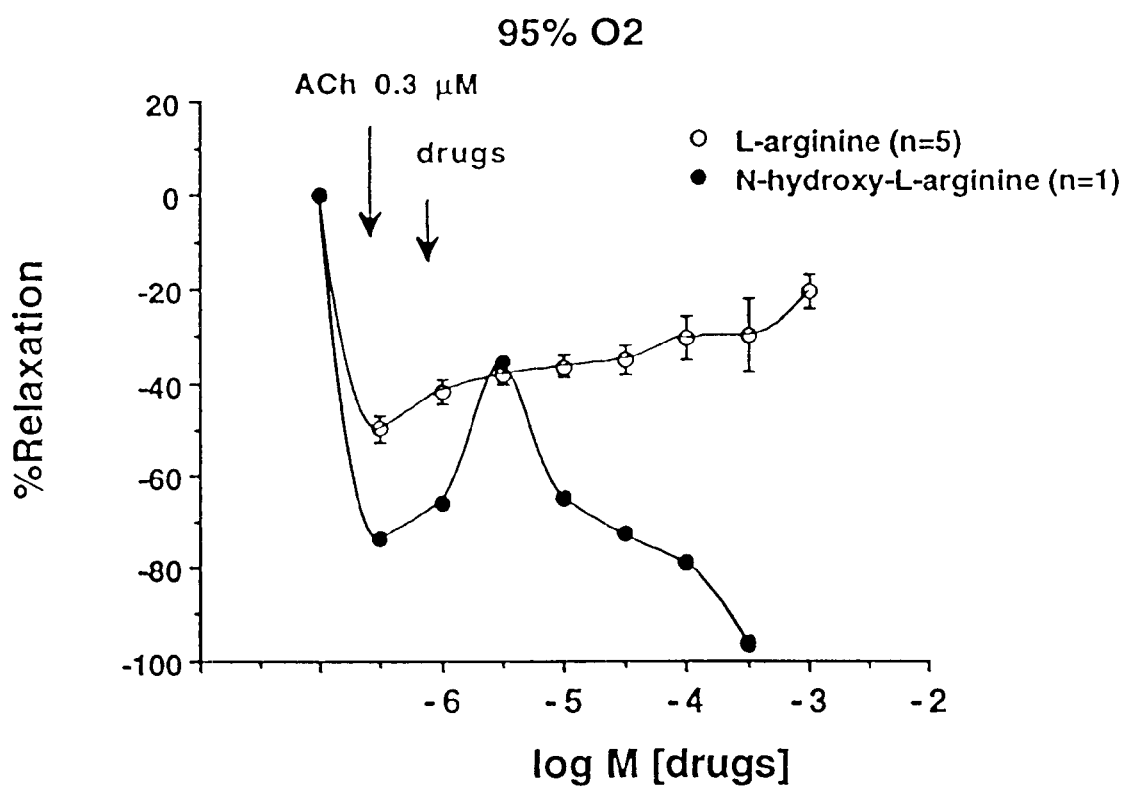

FIG. 11A shows that under normoxia conditions N-hydroxy-L-arginine is more potent than L-arginine to induce the relaxation of aortic rings isolated from diabetic rats. Tissues were incubated in physiological salt solution and bubbled with 95% $O_2$. Each sample was stimulated to relax by administration of 0.3 μM acetylcholine, and, after the tissue was allowed to recover, various concentrations of either L-arginine (open circles, total number of samples tested n=5); or N-hydroxy-L-arginine (closed circles, one sample tested n=1), were administered, and the relaxation of the tissue was again measured. In the x-axis, log M [drugs] corresponds to ten fold increases of either L-arginine or N-hydroxy-L-arginine from 100 nM (at −7) to 1000 μM (at −3). Data are expressed as mean±standard mean error of the percentage of total relaxation induced by 0.1 mM papaverine.

Figure 11B:
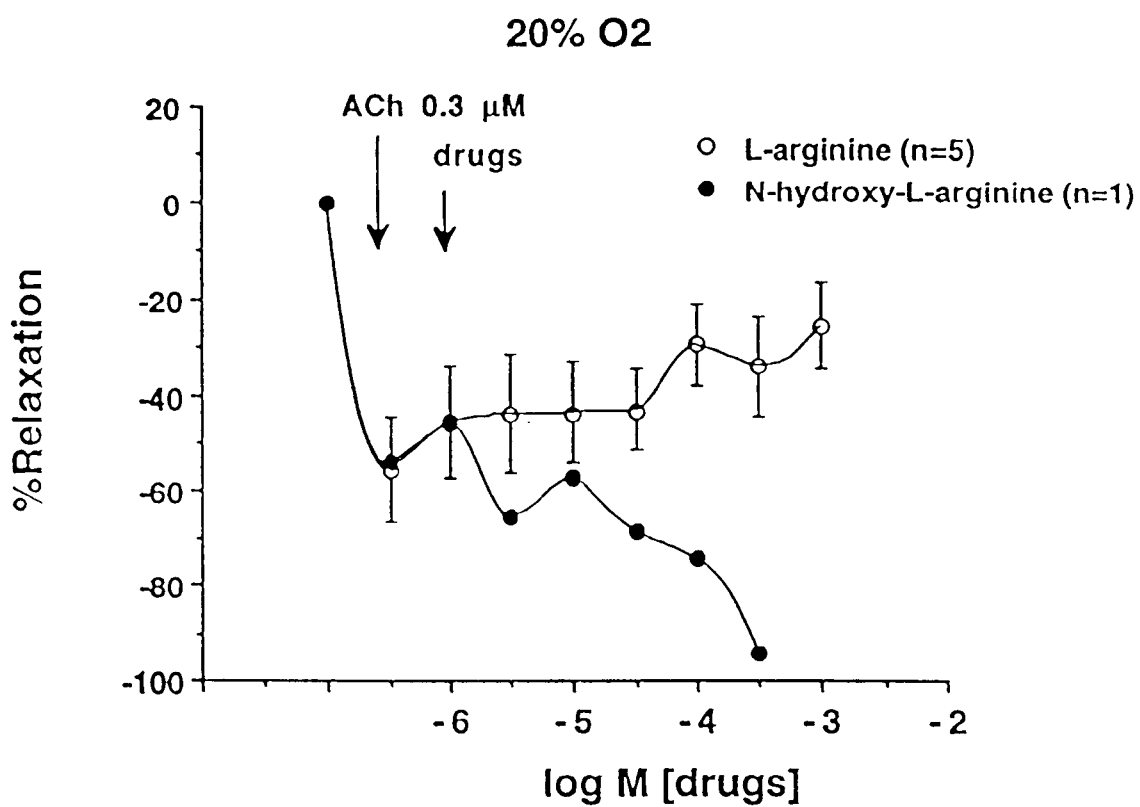

FIG. 11B shows that under normoxia conditions N-hydroxy-L-arginine is more potent than L-arginine to induce the relaxation of aortic rings isolated from diabetic rats. Tissues were incubated in physiological salt solution and bubbled with 20% $O_2$. Each sample was stimulated to relax by administration of 0.3 μM acetylcholine and, after the tissue was allowed to recover, various concentrations of either L-arginine (open circles, total number of samples tested n=5); or N-hydroxy-L-arginine (closed circles, one sample tested n=1), were administered and the relaxation of the tissue was again measured. In the x-axis, log M [drugs] corresponds to ten fold increases of either L-arginine or N-hydroxy-L-arginine from 100 nM (at −7) to 1000 μM (at −3). Data are expressed as mean±standard mean error of the percentage of total relaxation induced by 0.1 mM papaverine.

Figure 11C:
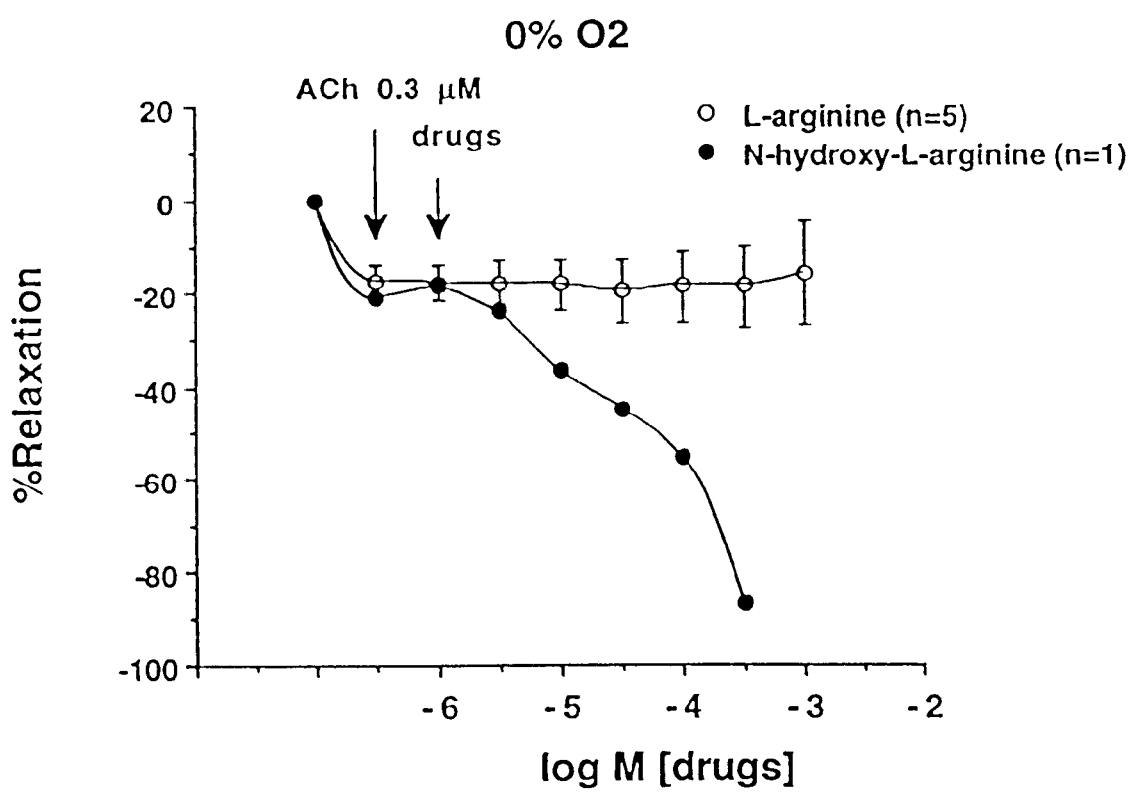

FIG. 11C shows that under hypoxia conditions N-hydroxy-L-arginine is more potent than L-arginine to induce the relaxation of aortic rings isolated from diabetic rats. Tissues were incubated in physiological salt solution in the presence of 0% $O_2$. Each sample was stimulated to relax by administration of 0.3 μM acetylcholine and, after the tissue was allowed to recover, various concentrations of either L-arginine (open circles, total number of samples tested n=5); or N-hydroxy-L-arginine (closed circles, one sample tested n=1), were administered, and the relaxation of the tissue was again measured. In the x-axis, log M [drugs] corresponds to ten fold increases of either L-arginine or N-hydroxy-L-arginine from 100 nM (at −7) to 1000 μM (at −3). Data are expressed as mean±standard mean error of the percentage of total relaxation induced by 0.1 mM papaverine.

Figure 12A:
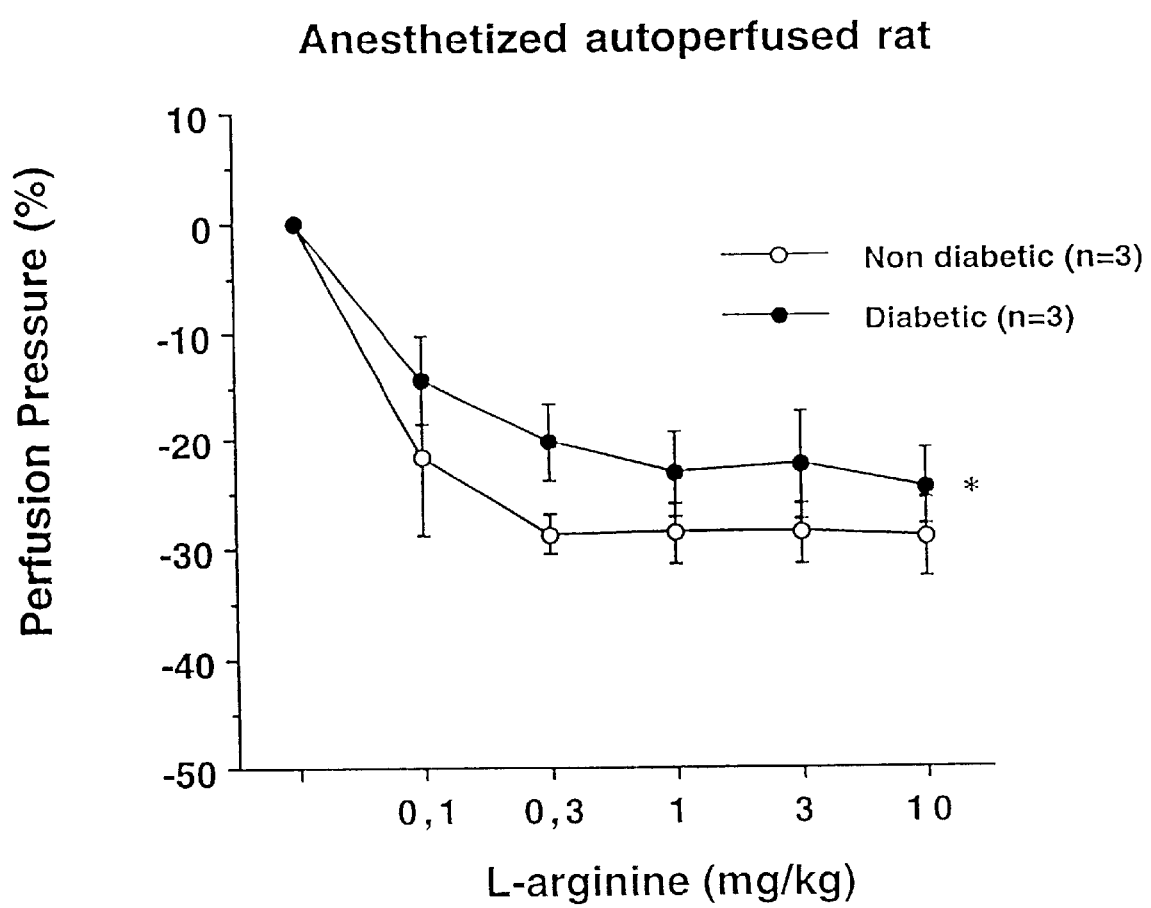

FIG. 12A shows that L-arginine decreases the perfusion pressure of non-diabetic more than the perfusion pressure of diabetic rats. The vasoactive response of the bolus infusion of increasing concentrations of L-arginine (ranging from 0.1 mg/kg to 10 mg/kg) to the left hindlimb of autoperfused (at a constant rate of 3.3 ml/min/kg) non-diabetic (open circles, total number of rats perfused n=3) or diabetic rats (closed circles, total number of rats perfused n=3) was measured. Data are expressed as mean±standard mean error of the percentage of pressure reached after the infusion of norepinephrine at 2 μg/min/kg. *P<0.05 compared to non-diabetic rats by AVONA analysis.

Figure 12B:
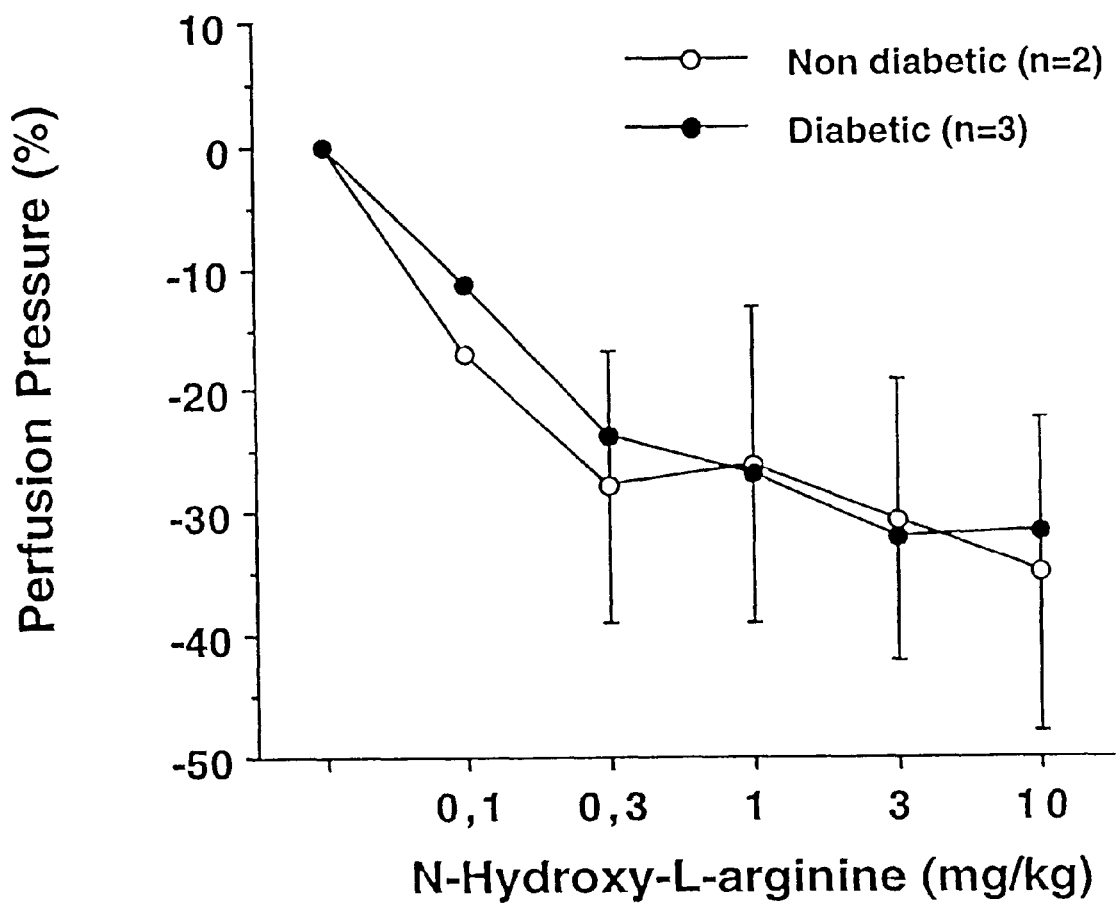

FIG. 12B shows that in the presence of increasing concentrations of N-hydroxy-L-arginine the perfusion pressure of non-diabetic or diabetic rats were very similar. The vasoactive response of the bolus infusion of increasing concentrations of N-hydroxy-L-arginine (ranging from 0.1 mg/kg to 10 mg/kg) to the left hindlimb of autoperfused (at a constant rate of 3.3 ml/min/kg) non-diabetic (open circles, total number of rats perfused n=2) or diabetic rats (closed circles, total number of rats perfused n=3) was measured. Data are expressed as mean±standard mean error of the percentage of previous pressure reached after the infusion of norepinephrine at 2 μg/min/kg.

DETAILED DESCRIPTION OF THE INVENTION

As used throughout the disclosure, the following terms, unless otherwise indicated, shall be understood to have the following meanings.

"N-hydroxyguanidine" refers to any N-hydroxylated guanidine compound that is a substrate for nitric oxide synthase "N-hydroxy-L-arginine" refers to $N^G$-hydroxy-L-arginine.

"Arginase" refers to the enzyme arginase, which converts arginine to ornithine and urea.

"Thromboxane A2 receptor antagonist" refers to any compound that reversibly or irreversibly inhibits thromboxane synthesis, and includes compounds which are the so-called thromboxane A2 receptor antagonists, thromboxane A2 antagonists, hromboxane A2/prostaglandin endoperoxide antagonists, TP-receptor antagonists, and thromboxane antagonists.

"Patient" refers to animals, preferably mammals, more preferably humans.

"Transurethral" or "intraurethral" refers to delivery of a drug into the urethra, such that the drug contacts and passes through the wall of the urethra and enters into the blood stream.

"Transdermal" refers to the delivery of a drug by passage through the skin and into the blood stream.

"Transmucosal" refers to delivery of a drug by passage of the drug through the mucosal tissue and into the blood stream.

"Penetration enhancement" or "permeation enhancement" refers to an increase in the permeability of the skin or mucosal tissue to a selected pharmacologically active agent such that the rate at which the drug permeates through the skin or mucosal tissue is increased.

"Carriers" or "vehicles" refers to carrier materials suitable for drug administration and include any such material known in the art such as, for example, any liquid, gel, solvent, liquid diluent, solubilizer, or the like, which is non-toxic and which does not interact with other components or the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO\bullet$), such that the biological activity of the nitrogen monoxide species is expressed at the intended site of action.

It has now been discovered that nitric oxide (NO) synthesis or endothelium-derived relaxing factor (EDRF) can be promoted in tissues under low oxygen conditions (i.e., conditions of hypoxia) by administering a therapeutically effective amount of at least one N-hydroxyguanidine compound that is a substrate for nitric oxide synthase. The N-hydroxyguanidine compound can be administered in a pharmaceutically acceptable carrier either alone or in combination with other active compounds. N-hydroxyguanidine compounds include, for example, N-aryl-N'-hydroxyguanidine (such as, for example, N-(4-chlorophenyl)N'-hydroxyguanidine)); nitrosated and/or nitrosylated N-aryl-N'-hydroxyguanidine; N-hydroxy-L-arginine; and analogs of N-hydroxy-L-arginine.

Analogs of N-hydroxy-L-arginine include, for example, $N^\omega$-hydroxy-homo-L-arginine; carboxylic ester of N-hydroxy-L-arginine (including, but not limited to, methyl, ethyl, propyl, isopropyl, butyl, isobutyl, t-butyl and benzoyl esters); N-α derivatives of N-hydroxy-L-arginine (including, but not limited to, methyl, ethyl, benzoyl derivatives such as for example, N-α methyl-$N^G$-hydroxy-L-arginine, N-α-benzoyl-$N^G$-hydroxy-L-arginine, N-α-benzoyl-$N^G$-hydroxy-L-arginine ethyl ester); $N^G$-hydroxy-agmatine; $N^G$-hydroxy-L-argininic acid; nitrosated and/or nitrosylated derivatives of N-hydroxy-L-arginine (such as, for example, nitrosated and/or nitrosylated N-hydroxy-L-arginine, nitrosated and/or nitrosylated $N^\omega$-hydroxy-homo-L-arginine, nitrosated and/or nitrosylated carboxylic ester of N-hydroxy-L-arginine; nitrosated and/or nitrosylated N-α derivatives of N-hydroxy-L-arginine, nitrosated and/or nitrosylated $N^G$-hydroxy-agmatine, and nitrosated and/or nitrosylated $N^G$-hydroxy-L-argininic acid). Preferred analogs of N-hydroxy-L-arginine include, for example, nitrosated and/or nitrosylated derivatives of N-hydroxy-L-arginine, more preferably nitrosated and/or nitrosylated N-hydroxy-L-arginine. The stable $N^G$-hydroxy-L-arginine-nitric oxide adduct has been characterized by Hecker et al, *Proc. Natl. Acad. Sci.*, 92:4671–4675 (1995) and shown to be pharmacologically active.

As described and exemplified herein, the administration of N-hydroxy-L-arginine was observed to increase basal and acetylcholine (ACh) stimulated production of nitric oxide (NO), as determined by measurement of cGMP in rabbit corpus cavernosum tissue. In addition, it was observed that N-hydroxy-L-arginine was more effective than L-arginine in increasing the production of NO and the attendant relaxation of corpus cavernosum tissue under hypoxic conditions. The effectiveness of N-hydroxy-L-arginine to promote corpus cavernosum tissue relaxation under hypoxic conditions demonstrates that N-hydroxy-L-arginine will be useful to treat clinical conditions associated with vasoconstriction due to low oxygen tension or the need to elevate endogenous levels of nitric oxide under hypoxic conditions.

Hypoxia is a condition in which there is a decreased supply of oxygen to peripheral tissues. At least three classes of hypoxias exist and can be distinguished based on their root causes. Arterial hypoxia and anemic hypoxia are characterized by lower than normal oxygen tension ($P_{O2}$) in arterial blood when the oxygen capacity and rate of blood flow are normal or even elevated. Arterial hypoxia results from exposure to pulmonary irritants that produce airway obstruction ranging from spasm or edema of the glottis to pulmonary edema (respiratory distress syndrome). Opiod narcotics and other drugs that depress respiration also produce arterial hypoxia. Anemic hypoxia results from a decreased concentration of functional hemoglobin, a reduced number of red cells, or chemically induced alterations in hemoglobin. Stagnant (hypokinetic) hypoxia is characterized by a decreased rate of blood flow, as in heart failure and uncorrected vasodilation.

Pieper et al (*J. Pharmacol. Exp. Ther.* 283(2): 684–691 (1997)) have shown that administering L-arginine in vitro can overcome a potential intracellular deficiency in nitric oxide production by diabetic endothelium. In the present invention, it was unexpectedly discovered and observed that administering N-hydroxy-L-arginine was more effective than L-arginine in the relaxation of aorta rings isolated from diabetic rats as compared to non-diabetic rats. The greater effectiveness of N-hydroxy-L-arginine to relax tissues isolated from diabetic species demonstrates that N-hydroxyguanidine compounds will be useful to treat clinical conditions associated with a deficient nitric oxide pathway.

N-Hydroxyguandinine compounds that are substrates for nitric oxide synthase have utility to treat essential hypertension, pulmonary hypertension, pulmonary diseases (including respiratory distress syndrome, asthma, bronchitis/emphysema, and chronic obstructive pulmonary disease), circulatory hypoxia (including heart failure, strokes, and shock), specific organ hypoxia (in which decreased circulation to a specific organ resulting in localized circulatory hypoxia can be due to organic arterial obstruction or can result as a consequence of vasoconstriction, e.g., Raynaud's Syndrome), localized hypoxia (which can result from venous obstruction and resultant congestions and reduced arterial blood inflow), edema (which increases the distance through which oxygen diffuses before it reaches the cells can also cause localized hypoxia), arterial diseases, central nervous system disorders, memory loss, and sexual dysfunctions (including hypoxic ischemia of the penis and female sexual dysfunctions). In addition, N-hydroxyguanidine compounds can be used to prevent and treat the same disorders that nitrovasodilators are now being clinically used to prevent and treat. Such nitrovasodilators include, but not limited to, glyceryl trinitrate (also known as nitroglycerin) and erythrityl tetranitrate, and such disorders include, for example, cardiovascular disorders, such as myocardial ischemia, congestive heart failure, and angina pectoris. N-Hydroxyguandinine compounds also have utility to treat clinical conditions associated with an abnormally high level of arginase activity, such as, heart disease, systemic hypertension, sexual dysfunctions, pulmonary hypertension, autoimmune diseases, chronic renal failure and cerebral vasospasm.

As used herein, "sexual dysfunction" includes any sexual dysfunction in a patient. The patient can be male or female. Sexual dysfunctions can include, for example, sexual desire disorders, sexual arousal disorders, orgasmic disorders and sexual pain disorders. Female sexual dysfunction refers to any female sexual dysfunction including, for example, sexual desire disorders, sexual arousal dysfunctions, orgasmic dysfunctions, sexual pain disorders, dyspareunia, and vaginismus. The female can be pre-menopausal or menopausal. Male sexual dysfunction refers to any male sexual dysfunction including, for example, male erectile dysfunction and impotence. In a preferred embodiment, "sexual dysfunctions" refer to sexual dysfunctions that are attributable to low oxygen conditions, including, but not limited to, sexual dysfunctions that are attributable to hypoxic ischemia, neuropathy, and arterial disease.

N-Hydroxyguanidine compounds, including pharmaceutically acceptable salts thereof, can be administered with any pharmaceutically acceptable carrier. The carrier should be pharmaceutically acceptable in the sense of being compatible with the other ingredients of the formulation and not deleterious to the recipient thereof. Administration can be sublingual, oral, rectal, vaginal, intranasal, intraocular, topical, transdermal, parenteral, intraarterial, intravenous, or buccal or by inhalation. The route of administration is at the discretion of the physician and takes into consideration the condition of the patient undergoing treatment. Formulations of N-hydroxyguanidine compounds can conveniently be presented in unit dosage form and can be prepared by any of the methods known in the pharmaceutical art.

N-hydroxyguanidine compounds that are substrates for nitric oxide synthase, can be administered with other compounds, such as vasoactive agents and/or thromboxane A2 receptor antagonists. For example, at least one N-hydroxyguanidine compound can be administered with at least one vasoactive agent; or at least one N-hydroxyguanidine compound can be administered with at least one thromboxane A2 receptor antagonist; or at least one N-hydroxyguanidine compound can be administered with at least one vasoactive agent and at least one thromboxane A2 receptor antagonist.

A vasoactive agent is any therapeutic agent that can relax vascular and non-vascular smooth muscle. Suitable vasoactive agents include, but are not limited to, long and short acting α-adrenergic blockers (such as, for example, phenoxybenzamine, dibenamine, doxazosin, terazosin, phentolamine, tolazoline, prazosin, trimazosin, yohimbine, moxisylyte); calcium channel blockers (such as, for example, nifedipine, veraparmil, diltiazem, gallopamil, niludipine, nimodipins, nicardipine); β-blockers (such as, for example, butixamine, dichloroisoproterenol, propanolol, alprenolol, bunolol, nadolol, oxprenolol, perbutolol, pinodolol, sotalol, timolol, metoprolol, atenolol, acebutolol, bevantolol, pafenolol, tolamodol); phosphodiesterase inhibitors (such as, for example, papaverine, zaprinast, sildenafil); adenosine, ergot alkaloids (such as, for example, ergotamine, ergotamine analogs, including, for example, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride); vasoactive intestinal peptides (such as, for example, peptide histidine isoleucine, peptide histidine methionine, substance P, calcitonin gene-related peptide, neurokinin A, bradykinin, neurokinin B); dopamine agonists (such as, for example, apomorphine, bromocriptine, testosterone, cocaine, strychnine); opioid antagonists (such as, for example, naltrexone); prostaglandins (such as, for example, alprostadil, prostaglandin $E_2$, prostaglandin $F_2$, misoprostol, enprostil, arbaprostil, unoprostone, trimoprostil, carboprost, limaprost, gemeprost, lantanoprost, ornoprostil, beraprost, sulpostrone, rioprostil); endothelin antagonists (such as, for example, bosentan, sulfonamide endothelin antagonists, BQ-123, SQ 28608); potassium channel activators (such as, for example nicorandil, pinacidal, cromakalim) and mixtures thereof. Preferred are combinations of N-hydroxy-L-arginine with α-adrenergic antagonists, phosphodiesterase inhibitors, prostaglandins, dopamine agonists, potassium channel activators or endothelin antagonists.

A thromboxane A2 receptor antagonists is any therapeutic agent that results in the relaxation of vascular and non-vascular smooth muscle. Suitable thromboxane A2 receptor antagonists include, but are not limited to, YM 158 (3-[4-tert-butylthiazol-2-yl)methoxy]-5'-[3-(4-chlorobenzenesulfonyl)propyl]-2'-(1H-tetrazol-5-ylmethoxy)benzanilide monosodium salt monohydrate)); Z-335 (1H-indene-5-acetic acid, 2((((4-chlorophenyl) sulphonyl)amino)methyl)-2,3-dihydro, monosodium salt)); KY-234; domitroban calcium hydrate; KT2-962 (1-azulenesulfonic acid), 3-(4-(((4-chlororphenyl)sulfonyl) amino)butyl)-6-(1-methylethyl)-monosodium salt)); camonagrel; glibenclamide; GR 32191 (([1R-[1α(Z), 2β,3β,5α]]-(+)-7-[5-([1,1'-biphenyl]-4-ylmethoxy)-3-hydroxy-2-(1 piperidinyl) cyclopentyl]-4-++++heptonoic acid); ZD 9583 (((4Z)-6-[(2S,4S,5R)-2-(1-[2-cyano-4-methylphenoxyl]-1-methylethyl)-4-(3-pyridyl)-1,3-dioxan-5-yl]hex-4-acid)); DT-TX 30 SE ((E-6-(4-2-(4-chlorobenzenesulphonylamino)-ethyl)phenyl)-6-(3-pyridyl)-hex-5-enoic acid)); BM 13505; BM 13177; SQ 29548; BAY u3405 ((3R-[[4-flourophenyl)sulphonyl] amino]-1,2,3,4,-tetrahydro-9H-carbozole-9-proponic acid)); ON-579; cinnamophilin (((8R,8S)-4,4'-dihydroxy-3,3'-dimethoxy-7-oxo-8,8'-neolignan)); ZD 1542 ((4(Z)-6-[2S, 4S,5R)-2-[1-methyl-1-(2-nitro-4-tolyloxy)ethyl]-4-(3-pyridyl)-1,3-dioxan-5-yl]hex-4-enoic acid)); BMS-180,291 ([(+)-1S-(1α,2α,3α,4α)-2-[[3-[4-[(n-pentylamino) carbonyl]-2-oxazolyl]-7-oxabicyclo[2.2.1]hept-2-yl] methyl]benzene propanoic acid)); FCE 27262; DuP 753; KW-3635 ((sodium (E)-11-[2-(5,6-dimethyl-1-benzimidazolyl)ethylidene]-6,11-dihydrodiben[b,e]oxepin-2-carboxylate monohydrate)); vapiprost; SQ 30,741; GR 32191; and mixtures thereof. Preferred are combinations of N-hydroxy-L-arginine with SQ 29548 and YM 158.

When administered in vivo, the compounds and/or compositions of the invention may be administered in combination with pharmaceutically acceptable carriers and in dosages described herein. When the compositions of the present invention are administered as a mixture of at least one N-hydroxyguanidine compound and at least one vasoactive agent and/or at least one thromboxane A2 receptor antagonist they can also be used in combination with one or more additional compounds which are known to be effective against the specific disease state targeted for treatment. N-hydroxyguanidine compounds can be administered simultaneously with, subsequently to, or prior to administration of the vasoactive agents(s) and/or thromboxane A2 receptor antagonist(s) and/or other additional compound(s).

The compounds and/or compositions of the invention can be administered by any available and effective delivery systems including, but not limited to, orally, bucally, parenterally, by inhalation spray, by topical application, by injection into the corpus cavernosum tissue, by transurethral drug delivery, transdermally, rectally or vaginally in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques. Transdermal drug administration, which is well known to one skilled in the art, involves the delivery of pharmaceutical agents via percutaneous passage of the drug into the systemic circulation of the patient. Topical administration may also involve transdermal patches or iontophoresis devices. Other components can also be incorporated into the transdermal patches as well. For example, compositions and/or transdermal patches may be formulated with one or more preservatives or bacteriostatic agents including, for example, methyl hydroxybenzoate, propyl hydroxybenzoate, chlorocresol, benzalkonium chloride, and the like.

Solid dosage forms for oral administration may include capsules, tablets, effervescent tablets, pills, powders, granules and gels. In such solid dosage forms, the active compounds may be admixed with at least one inert diluent such as sucrose, lactose or starch. Such dosage forms may also comprise, as in normal practice, additional substances other than inert diluents, e.g., lubricating agents such as magnesium stearate. In the case of capsules, tablets, effervescent tablets, and pills, the dosage forms may also comprise buffering agents. Soft gelatin capsules can be prepared to contain a mixture of the active compounds and/or compositions of the invention and vegetable oil. Hard gelatin capsules can contain granules of the active compound and/or compositions in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Dosage forms for topical administration of the compounds and/or compositions of the present invention can include creams, sprays, lotions, gels, ointments, coatings for condoms, and the like. Administration of the cream or gel may be accompanied by use of an applicator or by transurethral drug delivery using a syringe with or without a needle or penile insert or device, and is within the skill of the art. Typically a lubricant and/or a local anesthetic for desensitization can also be included in the formulation or provided for use as needed. Lubricants include, for example, K-Y jelly (available from Johnson & Johnson) or a lidocaine jelly, such as Xylocaine 2% jelly (available from Astra Pharmaceutical Products). Local anesthetics include, for example, novocaine, procaine, tetracaine, benzocaine and the like.

The compounds and/or compositions of the invention will typically be administered in a pharmaceutical composition containing one or more selected carriers or excipients. Suitable carriers include, for example, water, silicone, waxes, petroleum jelly, polyethylene glycol, propylene glycol, liposomes and sugars. The compositions can also include one or more permeation enhancers including, for example, dimethylsulfoxide (DMSO), dimethyl formamide (DMF), N,N-dimethylacetamide (DMA), decylmethylsulfoxide (C10MSO), polyethylene glycol monolaurate (PEGML), glyceral monolaurate, lecithin, 1-substituted azacycloheptan-2-ones, particularly 1-N-dodecylcyclazacylcoheptan-2-ones (available under the trademark Azone from Nelson Research & Development Co., Irvine, Calif.), alcohols and the like.

Suppositories for rectal or vaginal administration of the compounds and/or compositions of the invention can be prepared by mixing the drug with a suitable nonirritating excipient such as cocoa butter and polyethylene glycols which are solid at room temperature but liquid at rectal or vaginal temperature, such that they will melt in the rectum and release the drug.

Injectable preparations, for example, sterile injectable aqueous or oleaginous suspensions may be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Acceptable vehicles and solvents that can be used include, for example, water, Ringer's solution, and isotonic sodium chloride solution. Sterile fixed oils are also conventionally used as a solvent or suspending medium.

The compounds and/or compositions of the present invention can be formulated as neutral or acid salt forms. Pharmaceutically acceptable salts include, for example, those formed with free amino groups such as those derived from hydrochloric, hydrobromic, hydroiodide, phosphoric, sulfuric, nitrate, acetic, trifluoroacetic, citric, benzoic, fumaric, glutamic, lactic, malic, maleic, succinic, tartaric, p-toluenesulfonic, methanesulfonic acids, gluconic acid, glycolic acid and the like, and those formed with free carboxyl groups, such as those derived from sodium, potassium, ammonium, calcium, ferric hydroxides, isopropylamine, triethylamine, 2-ethylamino ethanol, histidine, procaine, and the like. The preferred pharmaceutically acceptable salts of N-hydroxy-L-arginine are hydrochloride, glutamate, butyrate, glycolate, trifluoroacetate and acetate and the most preferred salts are the acetate or trifluoroacetate salts.

"Therapeutically effective amount" refers to the amount of the N-hydroxyguanidine compound, vasoactive agent, and/or thromboxane A2 receptor antagonist that is effective to achieve its intended purpose. While individual patient needs may vary, determination of optimal ranges for effective amounts of the N-hydroxyguanidine compound, vasoactive agent and/or thromboxane A2 receptor antagonist is within the skill of the art. Generally, the dosage required to provide an effective amount of the composition, and which can be adjusted by one of ordinary skill in the art will vary, depending on the age, health, physical condition, sex, weight, extent of the dysfunction of the recipient, frequency of treatment and the nature and scope of the dysfunction.

The amount of a given vasoactive agent and/or thromboxane A2 receptor antagonist which will be effective in the treatment of a particular dysfunction or condition will depend on the nature of the dysfunction or condition, and can be determined by standard clinical techniques, including reference to Goodman and Gilman (9th Ed., 1995), The Pharmacological Basis of Therapeutics (9th Edition), McGraw-Hill (1996); The Physician's Desk Reference (49th Ed.); Medical Economics (1995); Drug Facts and Comparisons, (1993); and The Merck Index (12th Ed.), Merck & Co., Inc. (1996), the disclosures of each of which are incorporated herein by reference in their entirety. The precise dose to be used in the formulation will also depend on the route of administration, and the seriousness of the dysfunction or disorder, and should be decided by the physician and the patient's circumstances.

The usual doses of N-hydroxy-L-arginine administered to a patient is about 0.25 g/day to about 10 g/day, preferably about 2 g/day to about 4 g/day, more preferably about 3 g/day. The dose can optionally be administered orally at least one hour prior to sexual activity. Effective doses can be extrapolated from dose-response curves derived from in vitro or animal model test systems and are in the same ranges or less than as described for other commercially available compounds in, for example, the Physician's Desk Reference (49th Ed.).

The dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination. Thus, the dosage regimen actually employed may vary widely and therefore may deviate from the preferred dosage regimen set forth above.

Particularly preferred methods of administration of the N-hydroxyguanidine compounds and/or compositions for the treatment of male sexual dysfunction are oral, buccal, transdermal application, by injection into the corpus cavernosum, by transurethral administration, by inhalation or by the use of suppositories. The preferred methods of administration for female sexual dysfunction are oral, buccal, topical application, transdermal application, by inhalation or by the use of suppositories.

The present invention also provides pharmaceutical kits comprising one or more containers filled with one or more of the ingredients of the pharmaceutical compounds and/or compositions of the present invention, including, one or more N-hydroxyguanidine compounds and, optionally, one or more of the vasoactive agents and/or thromboxane A2 receptor antagonists described herein. Such kits can also include, for example, other compounds and/or compositions (e.g., permeation enhancers, lubricants), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The following examples are for purposes of illustration, and are not intended to limit the scope of the specification or claims.

The utility of N-hydroxy-L-arginine, an N-hydroxyguanidine compound, to promote the synthesis of NO was demonstrated in rabbit corpus cavernosum tissues (the erectile tissue of the penis) and rat aortic rings. Normal arterial oxygen tension measures as approximately 75–100 mm Hg, and normal venous oxygen tension measures as approximately 30–40 mm Hg. Experimentally equivalent oxygen concentrations for tissue culture are 20% oxygen (referred to herein as "normoxic"), which corresponds to approximately 140 mm Hg, to simulate arterial oxygen tension, and 5% oxygen (referred to herein as "hypoxic"), which corresponds to approximately 35 mm Hg, to simulate venous oxygen tension. Lower oxygen concentrations were also used as indicated. The preparation of the tissues for study was carried out as described herein.

Example 1

Preparation of Corpus Cavernosum Tissue

Rabbits were euthanized with an overdose of intravenous pentobarbital (60 mg/kg) and immediately exsanguinated. The entire penis was then removed and the corpus cavernosum tissue dissected free from the surrounding tunica albuginea and cut into strgips (3×3×7 mm). Corpus cavernosum tissues were maintained at 4–6° C. in M-400 solution (composition per 100 ml: mannitol, 4.19 g; $KH_2PO_4$, 0.205 g; $K_2HPO_4.3H_2O$, 0.97 g; KCl, 0.112 g; $NaHCO_3$, 0.084 g) until used. Corpus cavernosum tissues were typically used between 2 and 16 hrs from extraction.

Corpus cavernosum tissues prepared as described above, were subjected to the following tests to demonstrate that N-hydroxy-L-arginine is useful to promote the synthesis of nitric oxide even under conditions of low oxygen tension.

Example 2

Basal and Acetylcholine Stimulated Production of cGMP by Corpus Cavernosum Tissues Measurement of cyclic GMP in corpus cavernosal tissues was carried out as follows. Corpus cavernosal tissue strips were immersed in a 10 ml organ chamber containing physiological salt solution, maintained at 37° C. and aerated with 5% $CO_2$/95% air, pH 7.4. Each strip was incrementally stretched to optimal isometric tension, as determined by maximal contractile responses to 1 $\mu$M phenylephrine ((R)-3-hydroxy-α-[(methylamino)methyl]-benzenemethanol hydrochloride). The physiological salt solution was then replaced with one bubbled with either 20% oxygen or 0% oxygen and the tissues were then given 0.5 $\mu$M phenylephrine, 30 $\mu$M Zaprinast and 100 $\mu$M IBMX (3-isobutyl-1-methylxanthine, cAMP specific phosphodiesterase) and incubated for 15 minutes; after which time each tissue was incubated with the test drug (or control drug) at various concentrations or with vehicle (the buffer in which the drugs are delivered). Tissues were incubated for another 5 minutes then immediately frozen in liquid nitrogen and stored at −80° C. until extraction for cyclic nucleotide assay. Tissues were extracted by homogenization in 6% trichloroacetic acid followed by ether ($H_2O$-saturated) extraction and lyophilization. cGMP levels were determined by ELISA using a kit from Cayman Chemical Co. (Ann Arbor, Mich.).

Protein concentration in the corpus cavernosum tissue was determined using the Bio-Rad Protein Assay Kit microtiter plate assay procedure (Bio-Rad, Hercules, Calif.) with bovine serum albumin as the standard.

Figure 1:
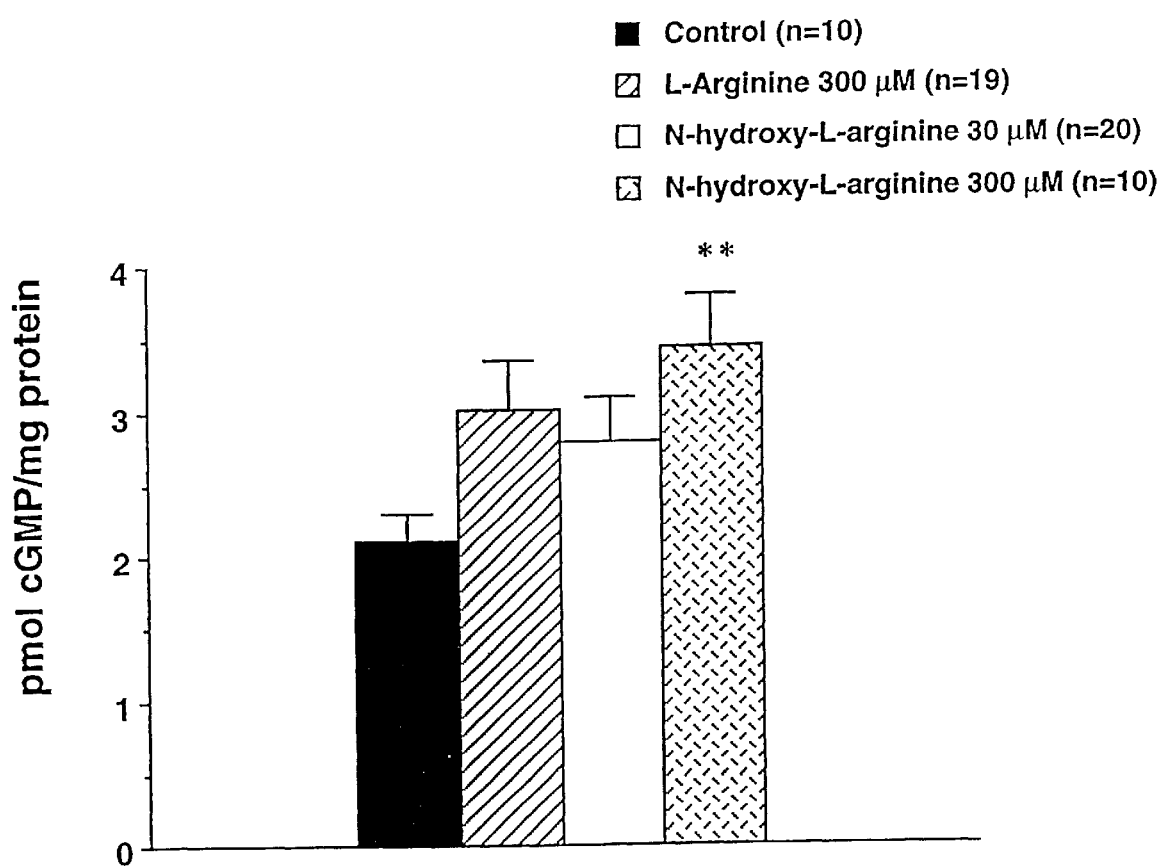
FIG. 1 is a measurement of cyclic GMP (cGMP) levels in rabbit corporal cavernosal tissues expressed as picomole of cGMP per milligram of protein. The prepared tissues were incubated with (a) vehicle control (filled bars) where a total of 10 samples were tested (n=10); (b) 300 $\mu$M L-arginine (hatched bars) where a total of 19 samples were tested (n=19); (c) 30 $\mu$M N-hydroxy-L-arginine (open bars) where a total of 20 samples were tested (n=20); and (d) 300 $\mu$M N-hydroxy-L-arginine (stippled bars) where a total of 10 samples were tested.

The basal level cGMP production by corpus cavernosum tissues under normoxic conditions was measured in the presence of vehicle, L-arginine and N-hydroxy-L-arginine. The measured concentrations of cGMP in picomoles were normalized based on milligrams of protein to provide a valid comparison between each tissue sample. As depicted in FIG. 1, under normoxic conditions the corpus cavernosum tissues are capable of producing cGMP without the addition of a drug or other stimulating agent (Control). Addition of 300 μM L-arginine or 30 μM N-hydroxy-L-arginine stimulated cGMP production approximately equally. Addition of 300 μM N-hydroxy-L-arginine, however, was effective to stimulate a higher concentration of cGMP production, and this increased amount of cGMP production was demonstrated to be statistically significant.

Figure 2A:
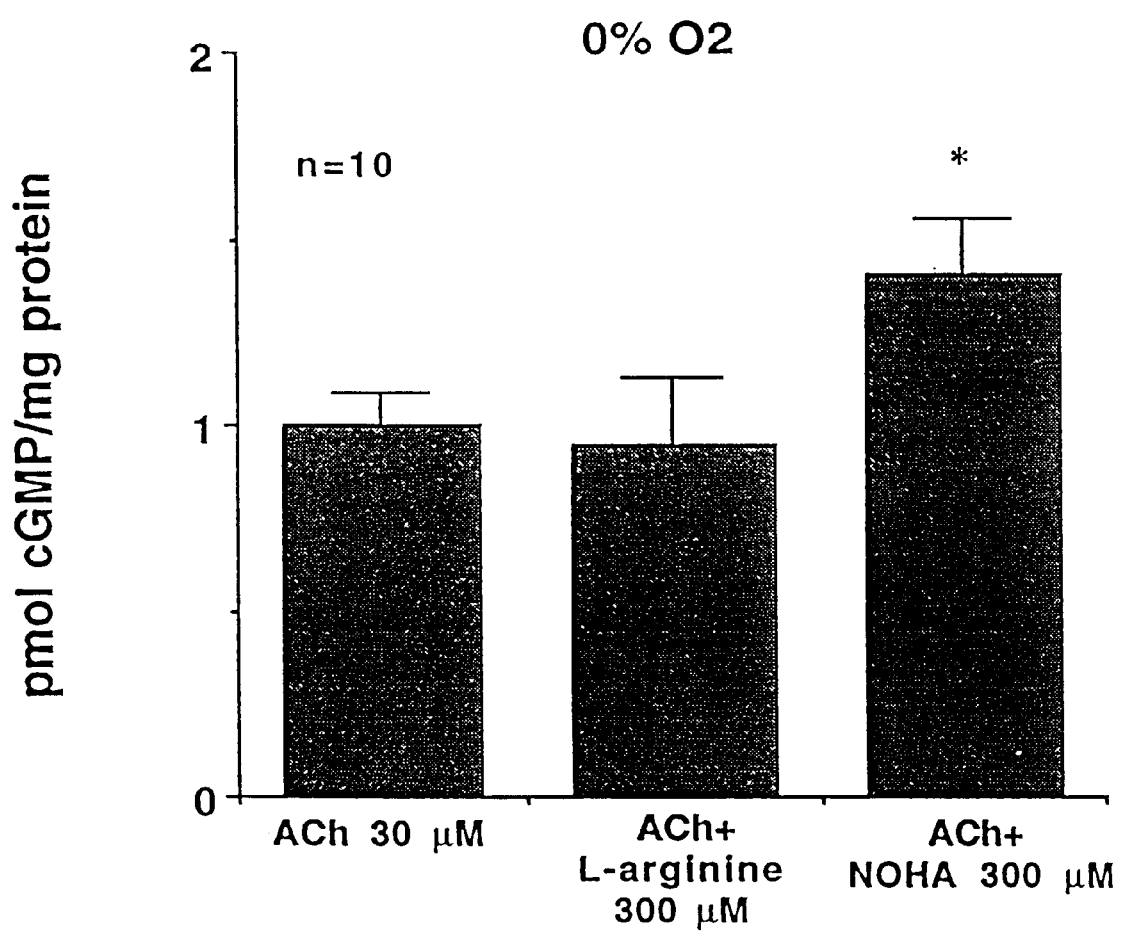
FIG. 2A compares the effects of L-arginine and N-hydroxy-L-arginine on cGMP levels (expressed as cGMP per milligram of protein) in rabbit cavernosal tissues stimulated with 30 $\mu$M acetylcholine (ACh) in the presence of 0% $O_2$. Tissues were incubated in physiological salt solution in the presence of 0% $O_2$ and were treated either with 30 $\mu$M ACh, or 300 $\mu$M L-arginine or 300 $\mu$M N-hydroxy-L-arginine in the presence of ACh. The cGMP levels for 10 samples of tissue were measured for each condition tested (n=10). *P<0.05 vs ACh alone using one way ANOVA analysis followed by Student-Newmann-Keuls post-hoc test.
Figure 2B:
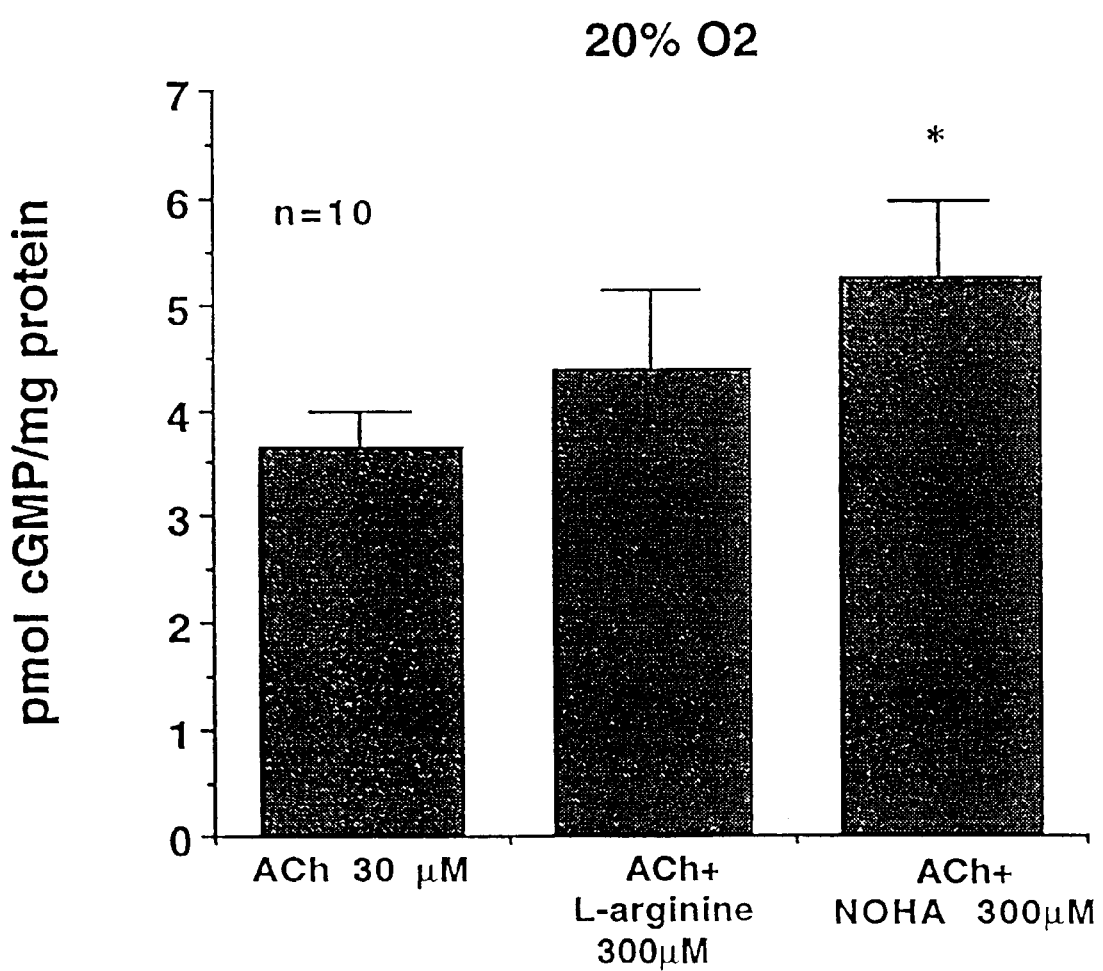
FIG. 2B shows the effects of L-arginine and N-hydroxy-L-arginine on cGMP levels in rabbit cavernosal tissues stimulated with 30 $\mu$M acetylcholine (ACh) in the presence of 20% $O_2$. Tissues were incubated in physiological salt solution and bubbled with 20% $O_2$ and were treated either with 30 $\mu$M ACh, or 300 $\mu$M L-arginine or 300 $\mu$M N-hydroxy-L-arginine in the presence of 30 $\mu$M ACh. *P<0.05 vs ACh alone using one way ANOVA analysis followed by Student-Newmann-Keuls post-hoc test.
Figure 3:
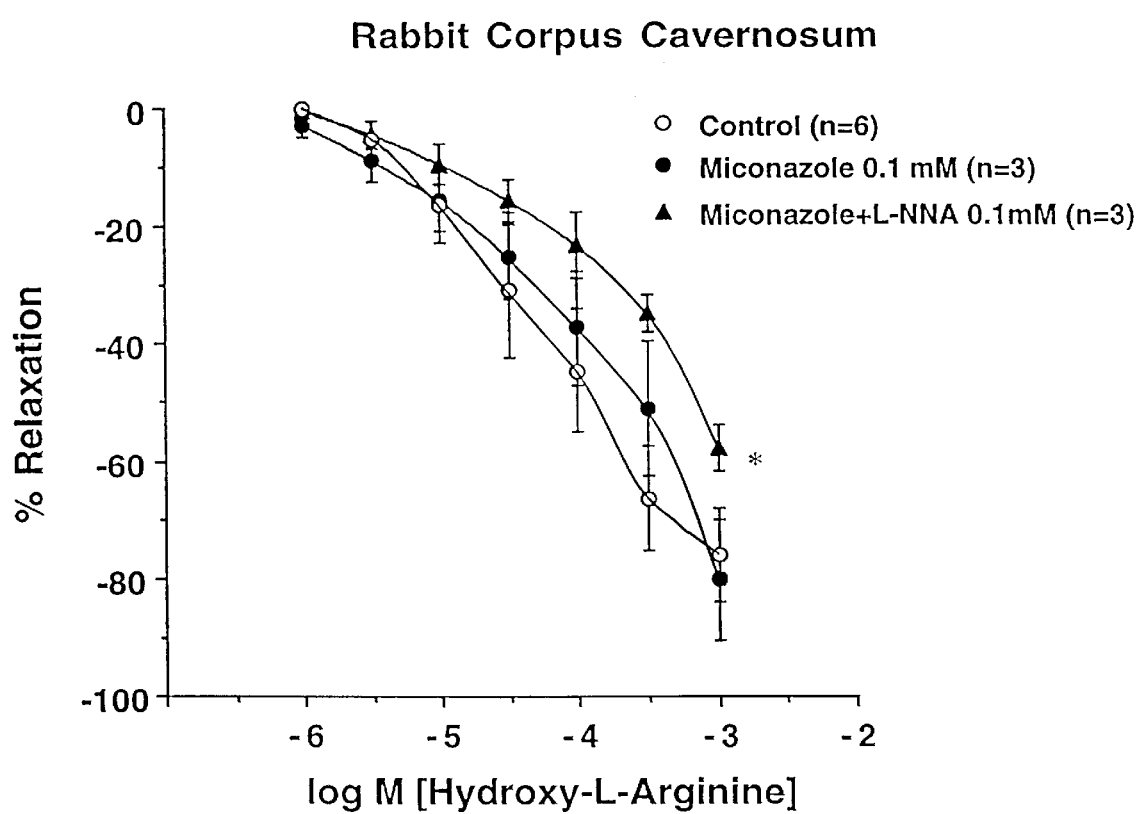
FIG. 3 shows that the inhibition of P450 metabolism, by the administration of miconazole does not inhibit N-hydroxy-L-arginine induced relaxation of isolated rabbit cavernosal tissues. Tissues were incubated in physiological salt solution and bubbled with 20% $O_2$ and were treated with increasing concentrations of N-hydroxy-L-arginine in the presence of vehicle alone (Control, open circles) where a total of 6 samples were tested (n=6); 0.1 mM miconazole (closed circles) where a total of 3 samples were tested (n=3); or 0.1 mM miconazole plus 0.1 mM $N^G$-nitro-L-arginine (L-NNA, an inhibitor of nitric oxide synthase) (closed triangles) where a total of 3 samples were tested (n=3). In the x-axis, log M [N-hydroxy-L-arginine] corresponds to ten fold increases of N-hydroxy-L-arginine from 1 $\mu$M (at −6) to 1000 $\mu$M (at −3). Data are expressed as mean±standard mean error of the percentage of total relaxation induced by 0.1 mM papaverine. *P<0.01 by AVONA analysis.

The level of cGMP production by corpus cavernosum tissues stimulated with acetylcholine was examined under conditions of normoxia and hypoxia (in this experiment, 0% oxygen), in the presence of L-arginine and N-hydroxy-L-arginine. The measured concentrations of cGMP in picomoles were normalized based on milligrams of protein to provide a valid comparison between each tissue sample. As depicted in FIGS. 2A and 2B, cGMP production was greatly reduced under conditions of low oxygen tension, in this case severe hypoxia of 0% oxygen. Comparable to the results depicted in FIG. 1, the results presented in FIGS. 2A and 2B show that under normoxia conditions (20% oxygen) and hypoxia, the addition of N-hydroxy-L-arginine results in a statistically significant increase in the concentration of cGMP compared to the basal values. Under the same conditions of normoxia and hypoxia, the administration of L-arginine was not effective to statistically increase the concentration of cGMP compared to the basal values. Thus, the administration of N-hydroxy-L-arginine has been demonstrated to be useful to promote the synthesis of nitric oxide even under conditions of low oxygen tension, in this case severe hypoxia of 0% oxygen.

Example 3

Preparation of Corpus Cavernosum Tissues for Relaxation Studies

Corpus cavernosum tissue was prepared as described in Example 1. For experimentation to measure relaxation of the tissue under various conditions, the corpus cavernosum tissues were then suspended in 10 ml organ chambers and bathed in a physiological salt solution, maintained at 37° C. and aerated with 5% $CO_2$/95% air, pH 7.4. Each corpus cavernosum tissue strip was incrementally stretched to optimal isometric tension as determined by the maximal contractile response to 1 μM phenylephrine. After several exchanges of fresh physiological solution, the media was bubbled with gas mixtures containing 5% $CO_2$, the indicated amount of oxygen (between 0% and 20%) and the remaining percentage was $N_2$, for thirty minutes. Corpus cavernosum tissues were then contracted with a submaximal concentration of phenylephrine, and the contraction was allowed to reach a steady state level. Once a steady state of muscle tension was reached, the tissue was exposed to various concentrations of test compounds, and the relaxation responses were recorded. Relaxation responses were expressed as a percentage of total relaxation induced by a supramaximal addition of papaverine (total loss of tone) at the end of the experiment. The data in FIGS. 3–6 are expressed as mean±standard mean error Example 4

Inhibition of P450 Does Not Inhibit N-hydroxy-L-arginine Induced Relaxation of Corpus Cavernosum Tissue The tissues were prepared according to Example 3 under normoxic conditions (20% oxygen). The percent relaxation of corpus cavernosum tissue induced by N-hydroxy-L-arginine in the presence of miconazole (an inhibitor of P450) was measured in order to determine if nitric oxide relaxation occurs via the P450 pathway. As can be seen from FIG. 3, the addition of miconazole to corpus cavernosum tissues in the presence of increasing concentrations of N-hydroxy-L-arginine does not significantly effect the relaxation of the tissues. The addition of L-NNA ($N^G$-nitro-L-arginine, an inhibitor of nitric oxide synthase), however, does decrease the effectiveness of N-hydroxy-L-arginine to relax the tissue. Thus, nitric oxide relaxation of corpus cavernosum tissue does not proceed via the P450 pathway.

Example 5

Inhibition of Nitric Oxide Synthase Inhibits N-hydroxy-L-arginine Induced Relaxation of Corpus Cavernosum Tissue The tissues were prepared according to Example 3 under normoxic conditions (20% oxygen). The percent relaxation of corpus cavernosum tissue induced by N-hydroxy-L-arginine in the presence of two different inhibitors of corporal tissue relaxation, L-NNA ($N^G$-nitro-L-arginine, a nitric oxide synthase inhibitor) and ODQ (1H-[1,2,4]oxadiazolo[4,3,a]quinoxalin-1-one, an inhibitor of soluble guanylate cyclase), was measured in order to demonstrate that N-hydroxy-L-arginine is converted to nitric oxide and citrulline by the action of nitric oxide synthase. As can be seen from FIG. 4A, the addition of either L-NNA or ODQ, significantly decreased the measured relaxation of the corpus cavernosum tissue even in the presence of increasing concentrations of N-hydroxy-L-arginine. Thus, the synthesis of nitric oxide from N-hydroxy-L-arginine is catalyzed by nitric oxide synthase.

In order to determine the specificity of the induced relaxation, the same experiment was repeated using varying concentrations of hydroxylamine instead of N-hydroxy-L-arginine. As seen from FIG. 4B, the addition of ODQ significantly decreased the relaxation of the corpus cavernosum tissue in the presence of increasing concentrations of hydroxylamine, while L-NNA had no effect. Thus hydroxylamine induces the relaxation of the tissue by a guanylate cyclase mediated pathway and nitric oxide synthase is not involved in the process.

Example 6

Relaxation of Corpus Cavernosum Tissue Under Normoxic and Hypoxic Conditions

The tissues were prepared according to Example 3 under normoxic conditions (20% oxygen) or hypoxic conditions (5% oxygen) as indicated below. Corpus cavernosum tissue was stimulated to relax either under normoxic or hypoxic conditions by the administration of acetylcholine. After the tissue was allowed to partially recover, it was again stimulated to relax by administering various concentrations of either L-arginine or N-hydroxy-L-arginine (arrow marked "drugs" in FIGS. 5A and 5B). Acetylcholine is a preganglionic neurotransmitter which stimulates relaxation of vascular tissues by stimulating endogenous nitric oxide production through the nitric oxide synthase pathway. Thus, intracellular stores of L-arginine and N-hydroxy-L-arginine are depleted following stimulation of the tissues with acetylcholine. As shown in FIGS. 5A and 5B, concentrations of N-hydroxy-L-arginine of 50 μM or greater was sufficient to induce relaxation of corpus cavernosum tissues under both normoxic and hypoxic conditions, and increasing concentrations N-hydroxy-L-arginine were increasingly effective. In contrast, concentrations of L-arginine as high as 1 mM were not effective to induce relaxation of corpus cavernosum tissues. These results demonstrate that N-hydroxy-L-arginine, but not L-arginine, can be taken into a cell and can then be converted to nitric oxide to induce the relaxation of the tissue even under hypoxic conditions.

Example 7

Relaxation of Corpus Cavernosum Tissues Under Various Oxygen Concentrations by N-hydroxy-L-arginine Corpus cavernosum tissue samples were prepared as described in Example 3 under the following oxygen concentrations: 0%, 1%, 2%, 5% and 20%. At oxygen concentrations of 0%, 1%, 2% and 5% administration of 1 mM L-arginine to the tissue had no measurable effect on tissue relaxation (data not shown). Administration of 1 mM N-hydroxy-L-arginine to the tissue at all oxygen concentrations resulted in significant relaxation of the tissue (FIG. 6). Thus, N-hydroxy-L-arginine has been shown to be effective to not only induce the synthesis of cGMP under hypoxic conditions (Example 2), but also to be effective to induce measurable relaxation of corpus cavernosum tissue samples.

Example 8

Preparation of Rat Aortic Segments

Diabetes was induced in rats by the administration of a single injection of steptozotocin (60 mg/kg; i.p). Diabetic rats remained untreated for a total of 8 weeks. Non-diabetic rats were those rats that did not receive the streptozotocin treatment.

Rats were anesthetized with diethyl ether and exsanguinated. The thoracic aorta was then removed and the tissue dissected free from the surrounding periadventitial fat and connective tissue, taking precautions to avoid touching the luminal surface. The tissue was cut into 8 segments, each approximately 3–4 mm in length. Rat aortic segments were maintained at 4–6° C. Krebs-bicarbonate buffer (composition per millimolar: NaCl, 120; KCl, 5.6; $MgCl_2$, 1.2; $NaH_2PO_4$, 1.2; dextrose, 10; $NaHCO_3$, 25; $CaCl_2$ 2.5; pH 7.4) until used. Aortic segments were typically used between 2 and 16 hrs from extraction.

For experimentation to measure relaxation of the tissue under various conditions, the rat aortic segments were suspended in 10 ml organ chambers and bathed in a physiological salt solution, maintained at 37 C and aerated with 5% $CO_2$/95% air, pH 7.4. Each aortic tissue strip was submitted to 1.5 g of resting tension. After several exchanges of fresh physiological solution, the media was bubbled with gas mixtures containing 5% $CO_2$, the indicated amount of oxygen (between 0% and 20%) and the remaining percentage was $N_2$, for thirty minutes. The aortic segments were then contracted with submaximal concentration of norepinephrine and the contraction as allowed to reach a steady state level. Once a steady state of muscle tension was reached, the tissue was exposed to various concentrations of test compounds and the relaxation responses were recorded. Relaxation responses were expressed as a percentage of total relaxation induced by a supramaximal addition of papaverine (total loss of tone) at the end of the experiment. In FIGS. 7–12, the data are expressed as mean±standard mean error.

Aortic segments prepared as described above, were subjected to the following tests to demonstrate that N-hydroxy-L-arginine is useful to promote the synthesis of nitric oxide even under conditions of low oxygen tension.

Example 9

L-arginine and N-hydroxy-L-arginine Induced Relaxation of Non-diabetic and Diabetic Aorta Segments.

The tissues were prepared according to Example 8 under normoxic conditions (95% oxygen). The percent contraction of aortic segments from non-diabetic and diabetic rats induced by L-arginine and N-hydroxy-L-arginine was measured. FIGS. 7A and 7B show that N-hydroxy-L-arginine was more effective in inducing relaxation in both non-diabetic and diabetic rats. FIG. 8 is a direct comparison of the N-hydroxy-L-arginine induced relaxation response of aortic segments obtained from non-diabetic and diabetic rats. At 1 μM N-hydroxy-L-arginine, the observed effect was significantly different and shows that N-hydroxy-L-arginine was more effective in inducing the relaxation of aortic segments obtained from diabetic rats.

Example 10

Inhibition of Nitric Oxide Synthase Inhibits N-hydroxy-L-arginine Induced Relaxation of Aorta Segments Isolated from Non-diabetic and Diabetic Rats The tissues were prepared according to Example 8 under normoxic conditions (20% oxygen). The percent contraction of rat aorta segments induced by N-hydroxy-L-arginine in the presence of a nitric oxide synthase inhibitor, L-NAME ($N^G$-nitro-L-arginine, 10 μM), was measured in order to demonstrate that N-hydroxy-L-arginine is converted to nitric oxide and citrulline by the action of nitric oxide synthase. As can be seen from FIGS. 9A and 9B, the addition of L-NAME significantly decreased the measured relaxation of the aorta segments obtained from non-diabetic and diabetic rats, respectively, even in the presence of increasing concentrations of N-hydroxy-L-arginine. Thus, the synthesis of nitric oxide from N-hydroxy-L-arginine is catalyzed by nitric oxide synthase.

Example 11

Acetylcholine Induced Relaxation of Aorta Segments Isolated from Non-diabetic and Diabetic Rats The tissues were prepared according to Example 8 under normoxic conditions (95% oxygen). The percent contraction of rat aorta segments induced by increasing concentrations of ACh in the presence of either 10 μM L-arginine or 10 μM N-hydroxy-arginine was measured in order to demonstrate the N-hydroxy-L-arginine is more effective in inducing the relaxation of rings isolated form diabetic rats. As can be seen from FIG. 10A neither L-arginine nor N-hydroxy-L-arginine in the presence of 10 nM to 10 μM ACh resulted in any change in the relaxation of the aorta segments isolated from non-diabetic rats. In contrast, N-hydroxy-L-arginine, in the presence of 10 nM to 10 μM ACh, increased the relaxation of rat aorta segments isolated from diabetic rats (FIG. 10B). Under the same conditions, L-arginine resulted in a decreased relaxation. These results demonstrate that N-hydroxy-L-arginine, is able to be taken up into cell more efficiently, and can then be converted into nitric oxide to induce the relaxation of the tissue isolated from diabetic rats.

Example 12

Relaxation of Aortic Segments Under Normoxic and Hypoxic Conditions

The tissues were prepared according to Example 8 under two normoxic conditions (95% and 20% oxygen) or hypoxic conditions (5% oxygen) as indicated below. Aortic segments from non-diabetic rats were stimulated to relax under either normoxic or hypoxic conditions by the administration of acetylcholine. After the tissue was allowed to partially recover, it was again stimulated to relax by administering various concentrations of either L-arginine or N-hydroxy-L-arginine (arrow marked "drugs" in FIGS. 11A, 11B and 11C). Acetylcholine is a preganglionic neurotransmitter which stimulates relaxation of vascular tissues by stimulating endogenous nitric oxide production through the nitric oxide synthase pathway. Thus intracellular stores of L-arginine and N-hydroxy-L-arginine are depleted following stimulation of the tissues with acetylcholine. As shown in FIGS. 11A, 11B and 11C, concentrations of N-hydroxy-L-arginine of 10 μM or greater were sufficient to induce relaxation of aortic segments under both normoxic and hypoxic conditions, and increasing concentrations N-hydroxy-L-arginine were increasingly effective. In contrast, concentrations of L-arginine as high as 1 mM were not effective to induce the relaxation of aortic segments. These results demonstrate that N-hydroxy-L-arginine, and not L-arginine, can be taken up into cell and can then be converted to nitric oxide to induce the relaxation of the tissue even under hypoxic conditions.

Example 13

Vasoactive Response of Anesthetized Autoperfused Rats

The left hindlimb of the anesthetized rats were perfused through the femoral artery at a constant rate of 3.3 ml/min/kg with blood from the carotid artery by means of a peristaltic pump. The vasoactive response induced by the bolus infusion of increasing concentrations of L-arginine or N-hydroxy-L-arginine into the left hindlimb of autoperfused non-diabetic or diabetic rats was determined by measuring the change in the perfusion pressure, which was previously elevated by a norepinephrine constant infusion (2 μg/min/kg). FIG. 12A shows the perfusion pressures resulting from the administration of 0.1 mg/kg to 10 mg/kg L-arginine to either non-diabetic or diabetic rats. At all concentrations of L-arginine, the pressure change was greater for the non-diabetic rats compared to diabetic rats. FIG. 12B shows that there was no difference in the perfusion pressure when increasing concentrations of N-hydroxy-L-arginine were administered to non-diabetic or diabetic rats.

The disclosure of each patent, patent application and publication cited or described in the specification is hereby incorporated by reference herein in its entirety.

Although the invention has been set forth in detail, one skilled in the art will appreciate that numerous changes and modifications can be made to the invention without departing from the spirit and scope thereof.

What is claimed is:

1. A method of treating an autoimmune disease in a patient in need thereof comprising administering a therapeutically effective amount of at least one N-hydroxyguanidine compound or a pharmaceutically acceptable salt thereof.

2. The method of claim 1, wherein the autoimmune disease is associated with an abnormally high level of arginase activity.

3. The method of claim 1, wherein the N-hydroxyguanidine compound is N-aryl-N'-hydroxyguanidine, a nitrosated N-aryl-N'-hydroxyguanidine, a nitrosylated N-aryl-N'-hydroxyguanidine, N-hydroxy-L-arginine, or an analog of N-hydroxy-L-arginine.

4. The method of claim 3, wherein the N-hydroxyguanidine compound is N-hydroxy-L-arginine.

5. The method of claim 3, wherein the N-hydroxy-L-arginine analog is $N^{\omega}$-hydroxy-homo-L-arginine, a carboxylic ester of N-hydroxy-L-arginine, a N-α derivative of N-hydroxy-L-arginine, $N^G$-hydroxy-agmatine, $N^G$-hydroxy-L-argininic acid, a nitrosated N-hydroxy-L-arginine, a nitrosylated N-hydroxy-L-arginine, a nitrosated $N^{\omega}$-hydroxy-homo-L-arginine, a nitrosylated $N^{\omega}$-hydroxy-homo-L-arginine, a nitrosated carboxylic ester of N-hydroxy-L-arginine, a nitrosylated carboxylic ester of N-hydroxy-L-arginine, a nitrosated N-α derivative of N-hydroxy-L-arginine, a nitrosylated N-α derivative of N-hydroxy-L-arginine, a nitrosated $N^G$-hydroxy-agmatine, a nitrosylated $N^G$-hydroxy-agmatine, a nitrosated $N^G$-hydroxy-L-argininic acid, or a nitrosylated $N^G$-hydroxy-L-argininic acid.

6. The method of claim 5, wherein the analog of N-hydroxy-L-arginine is the nitrosated N-hydroxy-L-arginine or the nitrosylated N-hydroxy-L-arginine.

7. The method of claim 6, wherein the nitrosated N-hydroxy-L-arginine or the nitrosylated N-hydroxy-L-arginine is an adduct of N-hydroxy-L-arginine with nitric oxide.

8. The method of claim 1, wherein the N-hydroxyguanidine compound is administered orally, parenterally, topically, vaginally, by inhalation, or by transurethral application.

9. The method of claim 1, further comprising administering to the patient at least one vasoactive agent or a pharmaceutically acceptable salt thereof.

10. The method of claim 9, wherein the vasoactive agent is an α-blocker, a calcium channel blocker, a β-blocker, a phosphodiesterase inhibitor, adenosine, an ergot alkaloid, a vasoactive intestinal peptide, a dopamine agonist, an opioid antagonist, a prostaglandin, an endothelin antagonist, a potassium channel activator or a mixture thereof.

11. The method of claim 1, further comprising administering to the patient at least one thromboxane A2 receptor antagonist or a pharmaceutically acceptable salt thereof.

12. The method of claim 11, wherein the thromboxane A2 receptor antagonist is YM 158 (3-[4-tert-butylthiazol-2-yl)methoxy]-5'-[3-(4-chlorobenzenesulfonyl)propyl]-2'-(1H-tetrazol-5-ylmethoxy)benzanilide monosodium salt monohydrate)); Z-335 (1H-indene-5-acetic acid, 2((((4-chlorophenyl)sulphonyl)amino)methyl)-2,3-dihydro, monosodium salt)); KY-234; domitroban calcium hydrate; KT2-962 (1-azulenesulfonic acid), 3-(4-(((4-chlorrophenyl)sulfonyl)amino)butyl)-6-(1-methylethyl)-monosodium salt)); camonagrel; glibenclamide; GR 32191 (([1R-[1α(Z),2β,3β,5α]]-(+)-7-[5-([1,1'-biphenyl]-4-ylmethoxy)-3-hydroxy-2-(1 piperidinyl) cyclopentyl]-4-++++heptonoic acid); ZD 9583 (((4Z)-6-[(2S,4S,5R)-2-(1-[2-cyano-4-methylphenoxy]-1-methylethyl)-4-(3-pyridyl)-1,3-dioxan-5-yl]hex-4-enoic acid)); DT-TX 30 5E ((E-6-(4-2-(4-chlorobenzenesulphonylamino)-ethyl)phenyl)-6-(3-pyridyl)-hex-5-enoic acid)); BM 13505; BM 13177; SQ 29548; BAY u3405 ((3R-[[4-flourophenyl)sulphonyl]amino]-1,2,3,4,-tetrahydro-9H-carbozole-9-proponic acid)); ON-579; cinnamophilin (((8R,8S)-4,4'-dihydroxy-3,3'-dimethoxy-7-oxo-8,8'-neolignan)); ZD 1542 ((4(Z)-6-[2S, 4S,5R)-2-[1-methyl-1-(2-nitro-4-tolyloxy)ethyl]-4-(3-pyridyl)-1,3-dioxan-5-yl]hex-4-enoic acid)); BMS-180,291 ([(+)-1S-(1α,2α,3α,4α)-2-[[3-[4-[(n-pentylamino)carbonyl]-2-oxazolyl]-7-oxabicyclo[2.2.1]hept-2-yl]methyl]benzene propanoic acid)); FCE 27262; DuP 753; KW-3635 ((sodium (E)-11-[2-(5,6-dimethyl-1-benzimidazolyl)ethylidene]-6,11-dihydrodiben[b,e]oxepin-2-carboxylate monohydrate)); vapiprost; SQ 30,741; or a mixture thereof.

13. A method of treating chronic renal failure in a patient in need thereof comprising administering a therapeutically effective amount of at least one N-hydroxyguanidine compound or a pharmaceutically acceptable salt thereof.

14. The method of claim 13, wherein the chronic renal failure is associated with an abnormally high level of arginase activity.

15. The method of claim 13, wherein the N-hydroxyguanidine compound is N-aryl-N'-hydroxyguanidine, a nitrosated N-aryl-N'-hydroxyguanidine, a nitrosylated N-aryl-N'-hydroxyguanidine, N-hydroxy-L-arginine, or an analog of N-hydroxy-L-arginine.

16. The method of claim 15, wherein the N-hydroxyguanidine compound is N-hydroxy-L-arginine.

17. The method of claim 15, wherein the N-hydroxy-L-arginine analog is $N^{\omega}$-hydroxy-homo-L-arginine, a carboxylic ester of N-hydroxy-L-arginine, a N-α derivative of N-hydroxy-L-arginine, $N^G$-hydroxy-agmatine, $N^G$-hydroxy-L-argininic acid, a nitrosated N-hydroxy-L-arginine, a nitrosylated N-hydroxy-L-arginine, a nitrosated $N^{\omega}$-hydroxy-homo-L-arginine, a nitrosylated $N^{\omega}$-hydroxy-homo-L-arginine, a nitrosated carboxylic ester of N-hydroxy-L-arginine, a nitrosylated carboxylic ester of N-hydroxy-L-arginine, a nitrosated N-α derivative of N-hydroxy-L-arginine, a nitrosylated N-α derivative of N-hydroxy-L-arginine, a nitrosated $N^G$-hydroxy-agmatine, a nitrosylated $N^G$-hydroxy-agmatine, a nitrosated $N^G$-hydroxy-L-argininic acid, or a nitrosylated $N^G$-hydroxy-L-argininic acid.

18. The method of claim 17, wherein the analog of N-hydroxy-L-arginine is the nitrosated N-hydroxy-L-arginine or the nitrosylated N-hydroxy-L-arginine.

19. The method of claim 18, wherein the nitrosated N-hydroxy-L-arginine or the nitrosylated N-hydroxy-L-arginine is an adduct of N-hydroxy-L-arginine with nitric oxide.

20. The method of claim 13, wherein the N-hydroxyguanidine compound is administered orally, parenterally, topically, vaginally, by inhalation, or by transurethral application.

21. The method of claim 13, further comprising administering to the patient at least one vasoactive agent or a pharmaceutically acceptable salt thereof.

22. The method of claim 21, wherein the vasoactive agent is an α-blocker, a calcium channel blocker, a β-blocker, a phosphodiesterase inhibitor, adenosine, an ergot alkaloid, a vasoactive intestinal peptide, a dopamine agonist, an opioid antagonist, a prostaglandin, an endothelin antagonist, a potassium channel activator or a mixture thereof.

23. The method of claim 13, further comprising administering to the patient at least one thromboxane A2 receptor antagonist or a pharmaceutically acceptable salt thereof.

24. The method of claim 23, wherein the thromboxane A2 receptor antagonist is YM 158 (3-[4-tert-butylthiazol-2-yl)methoxy]-5'-[3-(4-chlorobenzenesulfonyl)propyl]-2'-(1H-tetrazol-5-ylmethoxy)benzanilide monosodium salt monohydrate)); Z-335 (1H-indene-5-acetic acid, 2((((4-chlorophenyl)sulphonyl)amino)methyl)-2,3-dihydro, monosodium salt)); KY-234; domitroban calcium hydrate; KT2-962 (1-azulenesulfonic acid), 3-(4-(((4-chlororphenyl)sulfonyl)amino)butyl)-6-(1-methylethyl)-monosodium salt)); camonagrel; glibenclamide; GR 32191 (([1R-[1α(Z), 2β,3β,5α]]-(+)-7-[5-([1,1'-biphenyl]-4-ylmethoxy)-3-hydroxy-2-(1 piperidinyl) cyclopentyl]-4-++++heptonoic acid); ZD 9583 (((4Z)-6-[(2S,4S,5R)-2-(1-[2-cyano-4-methylphenoxy]-1-methylethyl)-4-(3-pyridyl)-1,3-dioxan-5-yl]hex-4-enoic acid)); DT-TX 30 5E ((E-6-(4-2-(4-chlorobenzenesulphonylamino)-ethyl)phenyl)-6-(3-pyridyl)-hex-5-enoic acid)); BM 13505; BM 13177; SQ 29548; BAY u3405 ((3R-[[4-flourophenyl)sulphonyl]amino]-1,2,3,4,-tetrahydro-9H-carbozole-9-proponic acid)); ON-579; cinnamophilin (((8R,8S)-4,4'-dihydroxy-3,3'-dimethoxy-7-oxo-8,8'-neolignan)); ZD 1542 ((4(Z)-6-[2S, 4S,5R)-2-[1-methyl-1-(2-nitro-4-tolyloxy)ethyl]-4-(3-pyridyl)-1,3-dioxan-5-yl]hex-4-enoic acid)); BMS-180,291 ([(+)-1S-(1α,2α,3α,4α)-2-[[3-[4-[(n-pentylamino)carbonyl]-2-oxazolyl]-7-oxabicyclo[2.2.1]hept-2-yl]methyl]benzene propanoic acid)); FCE 27262; DuP 753; KW-3635 ((sodium (E)-11-[2-(5,6-dimethyl-1-benzimidazolyl)ethylidene]-6,11-dihydrodiben[b,e]oxepin-2-carboxylate monohydrate)); vapiprost; SQ 30,741; or a mixture thereof.

25. A method of treating a cerebral vasospasm in a patient in need thereof comprising administering a therapeutically effective amount of at least one N-hydroxyguanidine compound or a pharmaceutically acceptable salt thereof; with the proviso that the N-hydroxyguanidine compound is not a carbimino hydroxyguanidine compound.

26. The method of claim 25, wherein the cerebral vasospasm is associated with an abnormally high level of arginase activity.

27. The method of claim 25, wherein the N-hydroxyguanidine compound is N-aryl-N'-hydroxyguanidine, a nitrosated N-aryl-N'-hydroxyguanidine, a nitrosylated N-aryl-N'-hydroxyguanidine, N-hydroxy-L-arginine, or an analog of N-hydroxy-L-arginine.

28. The method of claim 27, wherein the N-hydroxyguanidine compound is N-hydroxy-L-arginine.

29. The method of claim 27, wherein the N-hydroxy-L-arginine analog is $N^{\omega}$-hydroxy-homo-L-arginine, a carboxylic ester of N-hydroxy-L-arginine, a N-α derivative of N-hydroxy-L-arginine, $N^G$-hydroxy-agmatine, $N^G$-hydroxy-L-argininic acid, a nitrosated N-hydroxy-L-arginine, a nitrosylated N-hydroxy-L-arginine, a nitrosated $N^{\omega}$-hydroxy-homo-L-arginine, a nitrosylated $N^{\omega}$-hydroxy-homo-L-arginine, a nitrosated carboxylic ester of N-hydroxy-L-arginine, a nitrosylated carboxylic ester of N-hydroxy-L-arginine, a nitrosated N-α derivative of N-hydroxy-L-arginine, a nitrosylated N-α derivative of N-hydroxy-L-arginine, a nitrosated $N^G$-hydroxy-agmatine, a nitrosylated $N^G$-hydroxy-agmatine, a nitrosated $N^G$-hydroxy-L-argininic acid, or a nitrosylated $N^G$-hydroxy-L-argininic acid.

30. The method of claim 29, wherein the analog of N-hydroxy-L-arginine is the nitrosated N-hydroxy-L-arginine or the nitrosylated N-hydroxy-L-arginine.

31. The method of claim 30, wherein the nitrosated N-hydroxy-L-arginine or the nitrosylated N-hydroxy-L-arginine is an adduct of N-hydroxy-L-arginine with nitric oxide.

32. The method of claim 25, wherein the N-hydroxyguanidine compound is administered orally, parenterally, topically, vaginally, by inhalation, or by transurethral application.

33. The method of claim 25, further comprising administering to the patient at least one vasoactive agent or a pharmaceutically acceptable salt thereof.

34. The method of claim 33, wherein the vasoactive agent is an α-blocker, a calcium channel blocker, a β-blocker, a phosphodiesterase inhibitor, adenosine, an ergot alkaloid, a vasoactive intestinal peptide, a dopamine agonist, an opioid antagonist, a prostaglandin, an endothelin antagonist, a potassium channel activator or a mixture thereof.

35. The method of claim 25, further comprising administering to the patient at least one thromboxane A2 receptor antagonist or a pharmaceutically acceptable salt thereof.

36. The method of claim 35, wherein the thromboxane A2 receptor antagonist is YM 158 (3-[4-tert-butylthiazol-2-yl)methoxy]-5'-[3-(4-chlorobenzenesulfonyl)propyl]2'-(1H-tetrazol-5-ylmethoxy)benzanilide monosodium salt monohydrate)); Z-335 (1H-indene-5-acetic acid, 2((((4-chlorophenyl)sulphonyl)amino)methyl)-2,3-dihydro, monosodium salt)); KY-234; domitroban calcium hydrate; KT2-962 (1-azulenesulfonic acid, 3-(4-(((4-chlororphenyl)sulfonyl)amino)butyl)-6-(1-methylethyl)-monosodium salt)); camonagrel; glibenclamide; GR 32191 (([1R-[1α(Z),2β,3β,5α]]-(+)-7-[5-([1,1'-biphenyl]-4-ylmethoxy)-3-hydroxy-2-(1 piperidinyl) cyclopentyl]-4-++++heptonoic acid); ZD 9583 (((4Z)-6-[(2S,4S,5R)-2-(1-[2-cyano-4-methylphenoxy]-1-methylethyl)-4-(3-pyridyl)-1,3-dioxan-5-yl]hex-4-enoic acid)); DT-TX 30 5E ((E-6-(4-2-(4-chlorobenzenesulphonylamino)-ethyl)phenyl)-6-(3-pyridyl)-hex-5-enoic acid)); BM 13505; BM 13177; SQ 29548; BAY u3405 ((3R-[[4-flourophenyl)sulphonyl]amino]-1,2,3,4,-tetrahydro-9H-carbozole-9-proponic acid)); ON-579; cinnamophilin (((8R,8S)-4,4'-dihydroxy-3,3'-dimethoxy-7-oxo-8,8'-neolignan)); ZD 1542 ((4(Z)-6-[2S,4S,5R)-2-[1-methyl-1-(2-nitro-4-tolyloxy)ethyl]-4-(3-pyridyl)-1,3-dioxan-5-yl]hex-4-enoic acid)); BMS-180,291 ([(+)-1S-(1α,2α,3α,4α)-2-[[3-[4-[(n-pentylamino)carbonyl]-2-oxazolyl]-7-oxabicyclo[2.2.1]hept-2-yl]methyl]benzene propanoic acid)); FCE 27262; DuP 753; KW-3635 ((sodium (E)-11-[2-(5,6-dimethyl-1-benzimidazolyl)ethylidene]-6,11-dihydrodiben[b,e]oxepin-2-carboxylate monohydrate)); vapiprost; SQ 30,741; or a mixture thereof.

37. A method of treating a sexual dysfunction associated with an abnormally high level of arginase activity in a patient in need thereof comprising administering a therapeutically effective amount of at least one N-hydroxyguanidine compound or a pharmaceutically acceptable salt thereof.

38. The method of claim 37, wherein the patient is male.

39. The method of claim 37, wherein the patient is female.

40. The method of claim 37, wherein the N-hydroxyguanidine compound is N-aryl-N'-hydroxyguanidine, a nitrosated N-aryl-N'-hydroxyguanidine, a nitrosylated N-aryl-N'-hydroxyguanidine, N-hydroxy-L-arginine, or an analog of N-hydroxy-L-arginine.

41. The method of claim 40, wherein the N-hydroxyguanidine compound is N-hydroxy-L-arginine.

42. The method of claim 40, wherein the N-hydroxy-L-arginine analog is $N^{\omega}$-hydroxy-homo-L-arginine, a carboxylic ester of N-hydroxy-L-arginine, a N-α derivative of N-hydroxy-L-arginine, $N^G$-hydroxy-agmatine, $N^G$-hydroxy-L-argininic acid, a nitrosated N-hydroxy-L-arginine, a nitrosylated N-hydroxy-L-arginine, a nitrosated $N^{\omega}$-hydroxy-homo-L-arginine, a nitrosylated $N^{\omega}$-hydroxy-homo-L-arginine, a nitrosated carboxylic ester of N-hydroxy-L-arginine, a nitrosylated carboxylic ester of N-hydroxy-L-arginine, a nitrosated N-α derivative of N-hydroxy-L-arginine, a nitrosylated N-α derivative of N-hydroxy-L-arginine, a nitrosated $N^G$-hydroxy-agmatine, a nitrosylated $N^G$-hydroxy-agmatine, a nitrosated $N^G$-hydroxy-L-argininic acid, or a nitrosylated $N^G$-hydroxy-L-argininic acid.

43. The method of claim 42, wherein the analog of N-hydroxy-L-arginine is the nitrosated N-hydroxy-L-arginine or the nitrosylated N-hydroxy-L-arginine.

44. The method of claim 43, wherein the nitrosated N-hydroxy-L-arginine or the nitrosylated N-hydroxy-L-arginine is an adduct of N-hydroxy-L-arginine with nitric oxide.

45. The method of claim 37, wherein the N-hydroxyguanidine compound is administered orally, parenterally, topically, vaginally, by inhalation, or by transurethral application.

46. The method of claim 37, further comprising administering to the patient at least one vasoactive agent or a pharmaceutically acceptable salt thereof.

47. The method of claim 46, wherein the vasoactive agent is an α-blocker, a calcium channel blocker, a β-blocker, a phosphodiesterase inhibitor, adenosine, an ergot alkaloid, a vasoactive intestinal peptide, a dopamine agonist, an opioid antagonist, a prostaglandin, an endothelin antagonist, a potssium channel activator or a mixture thereof.

48. The method of claim 37, further comprising administering to the patient at least one thromboxane A2 receptor antagonist or a pharmaceutically acceptable salt thereof.

49. The method of claim 48, wherein the thromboxane A2 receptor antagonist is YM 158 (3-[4-tert-butylthiazol-2-yl)methoxy]-5'-[3-(4-chlorobenzenesulfonyl)propyl]-2'-(1H-tetrazol-5-ylmethoxyl)benzanilide monosodium salt monohydrate)); Z-335 (1H-indene-5-acetic acid, 2((((4-chlorophenyl)sulphonyl)amino)methyl)-2,3-dihydro, monosodium salt)); KY-234; domitroban calcium hydrate; KT2-962 (1-azulenesulfonic acid, 3-(4-(((4-chlororphenyl)sulfonyl)amino)butyl)-6-(1-methylethyl)-monosodium salt)); camonagrel; glibenclamide; GR 32191 (([1R-[1α(Z),2β,3β,5α]]-(+)-7-[5-([1,1'-biphenyl]-4-ylmethoxy)-3-hydroxy-2-(1 piperidinyl) cyclopentyl]-4-++++heptonoic acid); ZD 9583 (((4Z)-6-[(2S,4S,5R)-2-(1-[2-cyano-4-methylphenoxy]-1-methylethyl)-4-(3-pyridyl)-1,3-dioxan-5-yl]hex-4-enoic acid)); DT-TX 30 5E ((E-6-(4-2-(4-chlorobenzenesulphonylamino)-ethyl)phenyl)-6-(3-pyridyl)-hex-5-enoic acid)); BM 13505; BM 13177; SQ 29548; BAY u3405 ((3R-[[4-flourophenyl)sulphonyl]amino]-1,2,3,4,-tetrahydro-9H-carbozole-9-proponic acid)); ON-579; cinnamophilin (((8R,8S)-4,4'-dihydroxy-3,3'-dimethoxy-7-oxo-8,8'-neolignan)); ZD 1542 ((4(Z)-6-[2S,4S,5R)-2-[1-methyl-1-(2-nitro-4-tolyloxy)ethyl]-4-(3-pyridyl)-1,3-dioxan-5-yl]hex-4-enoic acid)); BMS-180,291 ([(+)-1S-(1α,2α,3α,4α)-2-[[3-[4-[(n-pentylamino)carbonyl]-2-oxazolyl]-7-oxabicyclo[2.2.1]hept-2-yl]methyl]benzene propanoic acid)); FCE 27262; DuP 753; KW-3635 ((sodium (E)-11-[2-(5,6-dimethyl-1-benzimidazolyl)ethylidene]-6,11-dihydrodiben[b,e]oxepin-2-carboxylate monohydrate)); vapiprost; SQ 30,741; or a mixture thereof.

* * * * *

UNITED STATES PATENT AND TRADEMARK OFFICE
Certificate

Patent No. 6,436,997 B1                                              Patented: August 20, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Inigo Saenz de Tejada, Madrid (ES); L. Gordon Letts, Dover, MA (US).

Signed and Sealed this Fourth Day of December 2007.

<div align="right">

WILLIAM R. DIXON, JR.
*Special Program Examiner*
Technology Center 1600

</div>